US010767213B2

(12) United States Patent
Eichmeyer et al.

(10) Patent No.: US 10,767,213 B2
(45) Date of Patent: *Sep. 8, 2020

(54) QUANTIFICATION OF VACCINE COMPOSITIONS

(71) Applicant: Boehringer Ingelheim Animal Health USA Inc., Duluth, GA (US)

(72) Inventors: Marc Allan Eichmeyer, Bondurant, IA (US); Michael B. Roof, Ames, IA (US); Merrill Lynn Schaeffer, St. Joseph, MO (US); Eric Martin Vaughn, Ames, IA (US); Kun Yang, Wynnewood, PA (US); Jeremy Richard Rush, Liberty, MO (US); Daniel John Murfin, St. Joseph, MO (US)

(73) Assignee: Boehringer Ingelheim Animal Health USA Inc., Duluth, GA (US)

( * ) Notice: Subject to any disclaimer, the term of this patent is extended or adjusted under 35 U.S.C. 154(b) by 30 days.

This patent is subject to a terminal disclaimer.

(21) Appl. No.: 15/456,013

(22) Filed: Mar. 10, 2017

(65) Prior Publication Data
US 2017/0253908 A1   Sep. 7, 2017

Related U.S. Application Data

(63) Continuation of application No. 14/194,380, filed on Feb. 28, 2014, now Pat. No. 9,624,527.
(Continued)

(51) Int. Cl.
*C12Q 1/37*  (2006.01)
*G01N 33/569*  (2006.01)
(Continued)

(52) U.S. Cl.
CPC ............... *C12Q 1/37* (2013.01); *C07K 7/06* (2013.01); *C07K 7/08* (2013.01); *C07K 14/001* (2013.01);
(Continued)

(58) Field of Classification Search
None
See application file for complete search history.

(56) References Cited

U.S. PATENT DOCUMENTS 6,703,023 B1   3/2004   Jestin et al.
7,148,015 B2   12/2006  Jestin et al.
(Continued)

FOREIGN PATENT DOCUMENTS

EP   2460818 A2    6/2012
TW   200940712 A  10/2009
(Continued)

OTHER PUBLICATIONS

Partial search report from corresponding PCT Application No. PCT/US2014/019643 dated Jun. 23, 2014.
(Continued)

*Primary Examiner* — Shanon A. Foley
(74) *Attorney, Agent, or Firm* — Richard Seeger; John Ezcurra

(57) ABSTRACT

The invention provides methods and mass-labeled peptides for use in said methods for quantifying the presence of a one or more viral proteins in a sample of a preparation containing agents which bind to said viral protein, using mass-spectroscopic analyses of the sample and standards containing known amounts of labeled and unlabeled signature peptides, in particular wherein said viral proteins are antigens in a vaccine for porcine circovirus.

18 Claims, 3 Drawing Sheets

Specification includes a Sequence Listing.

Related U.S. Application Data

(60) Provisional application No. 61/771,226, filed on Mar. 1, 2013.

(51) Int. Cl.
  *C07K 7/06* (2006.01)
  *C07K 14/00* (2006.01)
  *C07K 7/08* (2006.01)
  *G01N 33/68* (2006.01)
  *C07K 14/005* (2006.01)

(52) U.S. Cl.
  CPC ..... *C07K 14/005* (2013.01); *G01N 33/56983* (2013.01); *G01N 33/6848* (2013.01); *G01N 2333/01* (2013.01)

(56) References Cited

U.S. PATENT DOCUMENTS

| | | |
|---|---|---|
| 7,179,472 B2 | 2/2007 | Jestin et al. |
| 7,223,594 B2 | 5/2007 | Jestin et al. |
| 7,244,433 B2 | 7/2007 | Jestin et al. |
| 7,261,898 B2 | 8/2007 | Jestin et al. |
| 7,297,537 B2 | 11/2007 | Jestin et al. |
| 7,323,330 B2 | 1/2008 | Jestin et al. |
| 7,390,494 B2 | 6/2008 | Jestin et al. |
| 7,405,075 B2 | 7/2008 | Jestin et al. |
| 7,407,803 B2 | 8/2008 | Jestin et al. |
| 7,425,444 B2 | 9/2008 | Jestin et al. |
| 7,604,808 B2 | 10/2009 | Jestin et al. |
| 7,722,883 B2 | 5/2010 | Jestin et al. |
| 7,740,865 B2 | 6/2010 | Jestin et al. |
| 7,740,866 B2 | 6/2010 | Jestin et al. |
| 7,741,026 B2 | 6/2010 | Jestin et al. |
| 7,758,865 B2 | 7/2010 | Jestin et al. |
| 7,951,907 B2 | 5/2011 | Jestin et al. |
| 8,124,723 B2 | 2/2012 | Jestin et al. |
| 8,415,525 B2 | 4/2013 | Jestin et al. |
| 8,715,690 B2 | 5/2014 | Jestin et al. |
| 9,624,527 B2 * | 4/2017 | Eichmeyer ............ C12Q 1/37 |
| 2004/0076635 A1 | 4/2004 | Jestin et al. |
| 2004/0091502 A1 | 5/2004 | Jestin et al. |
| 2004/0161410 A1 | 8/2004 | Jestin et al. |
| 2004/0265848 A1 | 12/2004 | Jestin et al. |
| 2005/0008651 A1 | 1/2005 | Jestin et al. |
| 2005/0084497 A1 | 4/2005 | Jestin et al. |
| 2006/0083756 A1 | 4/2006 | Jestin et al. |
| 2006/0222663 A1 | 10/2006 | Jestin et al. |
| 2007/0041989 A1 | 2/2007 | Jestin et al. |
| 2007/0041990 A1 | 2/2007 | Jestin et al. |
| 2007/0048780 A1 | 3/2007 | Jestin et al. |
| 2007/0059324 A1 | 3/2007 | Jestin et al. |
| 2007/0059325 A1 | 3/2007 | Jestin et al. |
| 2007/0065925 A1 | 3/2007 | Jestin et al. |
| 2007/0110767 A1 | 5/2007 | Jestin et al. |
| 2007/0253971 A1 | 11/2007 | Jestin et al. |
| 2008/0233147 A1 | 9/2008 | Jestin et al. |
| 2009/0092627 A1 | 4/2009 | Jestin et al. |
| 2009/0123490 A1 | 5/2009 | Jestin et al. |
| 2009/0162918 A1 | 6/2009 | Jestin et al. |
| 2010/0074919 A1 | 3/2010 | Jestin et al. |
| 2010/0166791 A1 | 7/2010 | Jestin et al. |
| 2010/0172924 A1 | 7/2010 | Jestin et al. |
| 2010/0173786 A1 | 7/2010 | Brun et al. |
| 2010/0189732 A1 | 7/2010 | Jestin et al. |
| 2010/0189733 A1 | 7/2010 | Jestin et al. |
| 2010/0189734 A1 | 7/2010 | Jestin et al. |
| 2010/0189735 A1 | 7/2010 | Jestin et al. |
| 2010/0189736 A1 | 7/2010 | Jestin et al. |
| 2010/0189743 A1 | 7/2010 | Jestin et al. |
| 2010/0203072 A1 | 8/2010 | Jestin et al. |
| 2010/0209453 A1 | 8/2010 | Jestin et al. |
| 2010/0215690 A1 | 8/2010 | Jestin et al. |
| 2010/0221276 A1 | 9/2010 | Jestin et al. |
| 2010/0221283 A1 | 9/2010 | Jestin et al. |
| 2010/0226934 A1 | 9/2010 | Jestin et al. |
| 2011/0033489 A1 | 2/2011 | Jestin et al. |
| 2011/0135677 A1 | 6/2011 | Jestin et al. |
| 2012/0034630 A1 | 2/2012 | Jestin et al. |

FOREIGN PATENT DOCUMENTS

| | | |
|---|---|---|
| WO | 9929871 A2 | 6/1999 |
| WO | 03016861 A2 | 2/2003 |
| WO | 2007076520 A2 | 7/2007 |
| WO | 2008145763 A1 | 12/2008 |
| WO | 2014134561 A2 | 9/2014 |

OTHER PUBLICATIONS

Brun et al., "Isotope-labeled Protein Standards—Toward Absolute Quantitative Proteomics", Molecular & Cellular Proteomics, 6.12, [2007], pp. 2139-2149.

Fortin et al., "Multiple Reaction monitoring Cubed for Protein Quantification at the Low nanogram/Milliliter Level in Nondepleted Human Serum", Analytical Chemistry, vol. 81, No. 22 No. [2009], pp. 9343-9352.

Janecki et al., "A multiple reaction monitoring method for absolute quantification of the human liver alcohol dehydrogenase ADS1C1 isoenzyme", Analytical Biochemistry, vol. 369, [2007], pp. 18-26.

Kesihishian et al., Quantitative, Multiplexed Assays for Low Abundance Proteins in Plasma by Targeted Mass Spectrometry and Stable Isotope Dilution:, Molecular & Cellular Proteomics, 6.12, [2007}, pp. 2212-2229.

Kuhn et al., "Quantification of C-reactive protein in the serum of patients with rheumatoid arthritis using multiple reaction monitoring mass spectrometry and 13C-labeled peptide standards", Proteomics, vol. 4, [2004], pp. 1175-1186.

Kuzyk et al., "Multiple Reaction Monitoring-based, Multiplexed, Absolute Quantitation of 45 proteins in Human Plasma", Molecular & Cellular Proteomics, 8.8, [2009], pp. 1860-1877.

Lange et al., "Targeted Quantitative Analysis of *Sterptococcus pyogenes* Virulence Factors by Multiple Reaction Monitoring", Molecular & Cellular Proteomics, 7.8, [2008], pp. 1489-1500.

Lin, et al., "Quantification of Intermediate-Abundance proteins in Serum by Multiple Reaction Monitoring Mass Spectrometry in a Single-Quadrupole Ion Trap", Analytical Chemistry, vol. 78, No. 16, Aug. 2006, pp. 5762-5757.

Liu et al., "Two-dimensional liquid chromatography-tandem mass spectrometry coupled with isobaric tags for relative and absolute quantification (iTRAQ) labeling approach revealed first proteome profiles of pulmonary alveolar macrophages infected with porcine circovirus type 2". Jounral of Proteomics, vol. 79 [Feb. 2013], pp. 72-86.

McKay et al., "The development of multiple reaciton monitoring assays for liver-derived piasma proteins", Proteomics Clinical Application, vol. 1 [2007], pp. 1570-1581.

Metz et al., "Quality-control issues and approachs in vaccine development", Exper Review of Vaccines, vol. 8, No. 2 [2009], pp. 227-238.

Nicol et al., "Use of an Immunoaffinity-Mass Spectrometry-based Approach for the Quantification of protein Biomarkers from Serum Samples of Lunch Cancer Patients", Molecular & Cellular Proteomics, 7.1, [208], pp. 1974-1982.

Pierce et al., "Quantification of Immunoreactive Viral Influenza Proteins by Immunoaffinity Capture and Isotop-Dilution Liquid Chromatography Tandem Mass Spectrometry", Analytical Chemistry, vol. 83, [2001], pp. 4729-4737.

Qian et al., Enhanced Detection of Low Abundance Human Plasma Proteins Using a Tandem IgY12-SuperMix Immunoaffinity Separation Strategy, Molecular & Cellular Proteomics, 7.10, [2008], pp. 1963-1973.

Ramirez-Boo et al., "Quntitative proteomics by 2-DE, 16O/18O labeling and linear ion trap mass spectrometry analysis of lymph nodes from piglets inoculated by porcine circovirus type 2", Proteomics, vol. 11, No. 17, [Sep. 2011], pp. 3425-3469.

(56) References Cited

OTHER PUBLICATIONS

Whiteaker et al., "Integrated Pipelines for Mass Spectrometry-Based Discovery and Confirmation of Biomarkers Demonstrated in a Mouse Model of Breast Cancer", Journal of Proteome Research, vol. 6 [2007] pp. 3962-3975.
Williams et al. "Simultaneous quantification of hemagglutinin and neuraminidase of invluenze virus using isotope dilution mass spectrometry", Vaccine, vol. 30, [2012], pp. 2475-2482.
Williams et al., "Quantification of influenze virus hemagglutinins in complex mistures using isotope dilution tandem mass spectrometry", Vaccine, vol. 26, [2008], pp. 2510-2520.
International Search Report and Written Opinion for PCT/US2014/019643 dated Sep. 9, 2014.
Mallick et al., Computational prediction of proteotypic peptides for quantitative proteomics, Nat. Biotechnol., [2007], 25(1); pp. 125-131.
Schmidt and Urlaub, "Absolute Quantification of Proteins Using Standard Peptides and Multiple Reaction monitoring" in Quantitative Methods in Proteomics, Methods in Molecular Biology, vol. 893, Katrin Marcus (ed.), DOI 10.1007/978-1-61779-885-6_17, Springer Science+Business Media, LLC 2012.
Nawagitgul et al., "open reading fram 2 of porcine circovirus type 2 encodes a major capsid protein" J. Gen. Virol. 2000' 81: pp. 2281-2287.
Desiderio and Kai, Preparation of stable isotope-incorporated peptide internal standards for field desorption mass spectrometry quantificatio of peptides in biologic tissue, Biomed. Mass. Spectrom. 9183; 10(8); pp. 471-479.
Tian et al., Development of Multiplexed Microfluidic Proteomic Reactor and Its Application fo Studying Protein-Protein Interactions. Anal. Chem., [2001]; 83; pp. 4095-4102.
Morozov et al., "Detection of a Novel Strain of Porcine Circovirus in Pigs with Postweaning Multisystemic Wasting Syndrome", J. Clin. Microbiol., 1998; 36(9); pp. 2535-2541.
Kamp et al., eds. "Protein structure analysis: Preparation, characterization, and microsequencing." Springer Science & Business Media, 2000, pp. 45-47.
Kong, "Spectrometry for Complex Natural Products." China Medical Science Press, 2012, Chapter 4, pp. 86-88.
Li et al., "Quantification of endostar in rat plasma by LC-MS/MS and its application in a pharmacokinetic study." Journal of pharmaceutical and biomedical analysis 70 (2012): 505-511.
Lou, Zhongzi, et al. "Expression and antigenicity characterization for truncated capsid protein of porcine circovirus type 2." Canadian journal of veterinary research 75.1 (2011): 61-64.

* cited by examiner (a)

```
                        MTYPRRRYRRRRHRPRSHLGQILRRRPWLVHPRHRYRWRRKNGIFNTRLS
                                 10        20        30        40        50
PCV2 2a ORF2 vaccine    MTYPRRRYRRRRHRPRSHLGQILRRRPWLVHPRHRYRWRRKNGIFNTRLS    50
Opt. PCV2 2b ORF2-49836 MTYPRRRYRRRRHRPRSHLGQILRRRPWLVHPRHRYRWRRKNGIFNTRLS    50

RTFGYTXKXTTVXTPSWAVDMMRFNIXDFXPPGGGXNXXSXPFEYYRIRK
                                 60        70        80        90       100
PCV2 2a ORF2 vaccine    RTFGYTVKATTVTTPSWAVDMMRFNIDDFVPPGGGTNKISIPFEYYRIRK   100
Opt. PCV2 2b ORF2-49836 RTFGYTIKRTTVRTPSWAVDMMRFNINDFLPPGGGSNPRSVPFEYYRIRK   100

VKVEFWPCSPITQGDRGVGSXAVILDDNFVXKATALTYDPYVNYSSRHTI
                                110       120       130       140       150
PCV2 2a ORF2 vaccine    VKVEFWPCSPITQGDRGVGSTAVILDDNFVTKATALTYDPYVNYSSRHTI   150
Opt. PCV2 2b ORF2-49836 VKVEFWPCSPITQGDRGVGSSAVILDDNFVPKATALTYDPYVNYSSRHTI   150

XQPFSYHSRYFTPKPVLDXTIDYFQPNNKRNQLWLRLQTXXNVDHVGLGT
                                160       170       180       190       200
PCV2 2a ORF2 vaccine    PQPFSYHSRYFTPKPVLDSTIDYFQPNNKRNQLWLRLQTSRNVDHVGLGT   200
Opt. PCV2 2b ORF2-49836 TQPFSYHSRYFTPKPVLDGTIDYFQPNNKRNQLWLRLQTAGNVDHVGLGT   200

AFENSXYDQXYNIRVTMYVQFREFNLKDPPLXP
                                210       220       230
PCV2 2a ORF2 vaccine    AFENSKYDQDYNIRVTMYVQFREFNLKDPPLEP                    233
Opt. PCV2 2b ORF2-49836 AFENSIYDQEYNIRVTMYVQFREFNLKDPPLNP                    233
```

QUANTIFICATION OF VACCINE COMPOSITIONS

CROSS REFERENCE TO RELATED APPLICATION(S)

This application is a continuation of U.S. patent application Ser. No. 14/194,380, filed on Feb. 28, 2014 and published as U.S. Published Application No. 2014/0248603, and which is incorporated by reference in its entirety. U.S. patent application Ser. No. 14/194,380 claims the benefit of U.S. Provisional Application Ser. No. 61/771,226 which was filed Mar. 1, 2013, which is incorporated by reference in its entirety.

SEQUENCE LISTING

The instant application contains a Sequence Listing which has been submitted electronically in ASCII format and is hereby incorporated by reference in its entirety. Said ASCII copy, created on Mar. 10, 2017, is named 10-0154-US-3_SEQ_LISTING_10MAR2017.txt and is 22,522 bytes in size.

BACKGROUND OF THE INVENTION

To reduce animal stress and labor costs, it is desirable to vaccinate animals with as few doses as possible to achieve effectiveness. A combination vaccine against multiple pathogens that delivers an effective amount of antigen against each respective pathogen is desired. Practitioners and producers can achieve a combination vaccine by mixing antigens against multiple respective pathogens just prior to vaccination. But, such preparation in the field can introduce admixing errors, and there is no certainty that the combinations of antigens are compatible with one another.

It is desirable to have a premixed combination vaccine against multiple pathogens available so that labor costs and potential dosing errors are reduced and an effective dose of antigen against each respective pathogen is reliably delivered to a subject.

To reduce manufacturing costs, it is desirable to streamline vaccine production. For example, checking the quality of a cell culture for the desired immunogenic material prior to harvest or prior to admixing multiple immunogenic compositions together can reduce variability and waste.

To gain regulatory approval for a therapeutic immunogenic composition, e.g., a vaccine, as well as for safety reasons, a means of monitoring the antigen quantity and stability of the composition is required. Historically, that method has been ELISA-based. ELISA requires the availability of a suitable antibody for the antigen to be measured. But, ELISA-based methods can face certain obstacles: (1) suitable antibodies are not always available; and (2) these methods are not always able to reliably quantify and precisely quantify (e.g. ±10% deviation) complex biotherapeutics. This latter obstacle is especially problematic when multiple antigens are present in a vaccine.

However, for a combination vaccine to become a commercial product, the reference stability of the combined antigens must be ascertainable in the combination. That is, the amount of each respective antigen must be determinable over time after they are combined to ensure that the desired amount of each respective antigen is present in each dose.

In some combination vaccines, the individual vaccine preparations may contain elements that interfere with the detection of the other vaccine components using standard techniques. For example, a combination vaccine may contain a first and a second antigen, wherein the second antigen formulation may include serum from animals which have been exposed to an organism containing the first antigen, or which have been vaccinated with an antigen identical to or antigenically similar to the first antigen. In this situation, the first antigen may have elicited production of competing antibodies specific to the first antigen; thus, the serum present in the second antigen formulation may contain antibodies to the first antigen and these antibodies may be present in the combination vaccine. As a result, the standard immunological means for monitoring the reference stability of the first antigen in a single-component vaccine (i.e., ELISA) would be unable to adequately ascertain the stability of the resulting combination vaccine. In the absence of a suitable ELISA assay, the antigen stability and the efficacy of the vaccine would be determined in a clinical study in the host animal. The clinical study would entail vaccination of a statistically relevant number of animals followed by challenge. Clinical studies are expensive to perform, including the cost of animals, need for suitable housing (biocontainment), and testing of clinical samples collected during the study. An alternative means suitable for monitoring large scale manufacturing and for reliably determining the final concentrations of respective antigens in a combination vaccine are needed.

SUMMARY OF THE INVENTION

The invention provides methods and compositions, e.g., specific peptides that are preferably labelled, for use in said methods for quantifying the presence of a one or more target proteins, preferably viral proteins, in a sample, preferably of a preparation containing agents which bind to the target protein, using mass-spectroscopic analyses of the sample and preferably standards containing known amounts of labeled and unlabeled signature peptides.

In a preferred embodiment, the invention is a method of quantifying the presence of a one or more viral proteins in a sample of a preparation containing agents which bind to the viral protein, comprising
  (a) digesting the sample with a protease;
  (b) adding a known quantity of at least one stable-isotope-labeled signature peptide specific to at least one viral protein in the sample, wherein the signature peptides are pre-selected by determining that
    i. the signature peptides are specific to the protease digest of the viral protein to be quantified;
    ii. the signature peptides are specifically absent from the protease digest of the preparation in the absence of the viral protein;
    iii. the signature peptides produce a strong signal in a mass-spectrographic analysis; and
    iv. the signature peptides produce a distinguishable signal in a mass-spectrographic analysis;
  (c) running mass-spectroscopic analyses of the sample and standards containing known amounts of labeled and unlabeled signature peptides; and
  (d) determining the amount of viral protein in the vaccine preparation sample by comparing the results of the sample mass-spectroscopic analysis with the results of the standards.

In another preferred embodiment, the protein is ORF2 of a porcine circovirus (PCV).

In a further preferred embodiment, the protein is ORF2 of PCV2. the signature peptides are one or more of i. NVDHVGLGTAFENS[KC¹³N¹⁵], (SEQ ID NO: 4)
and ii. VEFWPCSPITQGD[RC¹³N¹⁵]. (SEQ ID NO: 24)

In another embodiment, protein is a mixture of ORF2s of PCV2 subtypes, e.g., PCV2a and PCV2b.

In still further preferred embodiments, the method further comprises, after protease digestion, immunopurifying the viral protein digest, or passing the preparation over a size-exclusion chromatographic column and selecting the fractions eluted from the column containing viral protein from fractions containing other compounds in the preparation, on the basis of molecular size.

In yet another embodiment, at least two stable-isotope-labeled signature peptides are used, wherein a first signature peptide is used for quantitation of the viral peptide in the preparation and a second signature peptide is used for qualitative determination of the stability of the peptide in the preparation.

Another embodiment is a method of making a vaccine preparation or immunogenic preparation containing one or more viral immunogens, wherein the vaccine or immunogenic preparation contains agents which bind to a viral protein in a first immunogenic composition, comprising using a multiple reaction monitoring-mass spectrometry (MRM-MS) for quantitative and qualitative assays for one or more preparations or quality control determinations. Immunogenic compositions may comprise viral antigens and/or bacterial antigens.

A still further preferred embodiment comprises methods as described above, wherein MRM-MS comprises
  a. digesting a sample of the vaccine or immunogenic preparation with a protease;
  b. adding a known quantity of at least one stable-isotope-labeled signature peptide specific to at least one viral protein to the sample, wherein the signature peptides are pre-selected by determining that
    i. the signature peptides are specific to the protease digest of the viral protein to be quantified;
    ii. the signature peptides are specifically absent from the protease digest of the preparation in the absence of the viral protein;
    iii. the signature peptides produce a strong signal in a mass-spectrographic analysis; and
    iv. the signature peptides produce a distinguishable signal in a mass-spectrographic analysis;
  c. running mass-spectroscopic analyses of the sample and standards containing known amounts of labeled and unlabeled signature peptides; and
  d. determining the amount of viral protein in the vaccine preparation sample by comparing the results of the sample mass-spectroscopic analysis with the results of the standards.

Another preferred embodiment comprises methods as described above wherein the running of the mass-spectroscopic analyses comprises:
  a. ionizing the sample;
  b. separating a plurality of ions according to their mass or mass-to-charge ratios; and
  c. detecting at least one ion corresponding to the viral protein.

In a particularly preferred embodiment, the invention is an isolated mass-labeled peptide selected from the group consisting of:

a. NVDHVGLGTAFENS[KC¹³N¹⁵], (SEQ ID NO: 4)

b. VEFWPCSPITQGD[RC¹³N¹⁵], (SEQ ID NO: 24)

c. SVPFEYY[RC¹³N¹⁵], (SEQ ID NO: 27)

d. HTITQPFSYHS[RC¹³N¹⁵], (SEQ ID NO: 15)

e. TFGYTV[KC¹³N¹⁵], (SEQ ID NO: 5)

f. ATTVTTPSWAVDMM[RC¹³N¹⁵], (SEQ ID NO: 6)

g. FNIDDFVPPGGGTNKISIPFEYY[RC¹³N¹⁵], (SEQ ID NO: 7)

h. ATALTYDPYVNYSS[RC¹³N¹⁵], (SEQ ID NO: 8)

i. HTIPQPFSYHSR, (SEQ ID NO: 9)

j. YFTPKPVLDSTIDYFQPNN[KC¹³N¹⁵], (SEQ ID NO: 10)

k. VTMYVQF[RC¹³N¹⁵], (SEQ ID NO: 11)

l. MTTVTTPSWNVDMM[RC¹³N¹⁵], (SEQ ID NO: 12)

m. FNINDFLPPGGGSNPLTVPFEYY[RC¹³N¹⁵], (SEQ ID NO: 13)

n. ANALTYDPYVNYSS[RC¹³N¹⁵], (SEQ ID NO: 14)

o. YFTP[KC¹³N¹⁵], (SEQ ID NO: 16)

p. PVLD[RC¹³N¹⁵], (SEQ ID NO: 17)

q. LQTTGNVDHVGLGTAFENSIYDQDYNI[RC¹³N¹⁵], (SEQ ID NO: 18)

r. ITMYVQF[RC¹³N¹⁵], (SEQ ID NO: 19)

s. EFNL[KC¹³N¹⁵], (SEQ ID NO: 20)

t. DPPLNP[KC¹³N¹⁵], (SEQ ID NO: 21)

u. YFTPK PVLD[RC¹³N¹⁵], (SEQ ID NO: 22)

v. EFNLK DPPLNP[KC¹³N¹⁵], (SEQ ID NO: 23)

w. VEFWPCSPITQGD[RC¹³N¹⁵], (SEQ ID NO: 24)

x. GVGSTAVILDDNFVT[KC¹³N¹⁵], (SEQ ID NO: 25)
and combinations thereof.

BRIEF DESCRIPTION OF THE DRAWINGS

FIG. 3: Amino acid sequence alignment of PCV2a and PCV2b ORF2s. Signature peptides for the sequences are indicated as follows:

Figure 1:
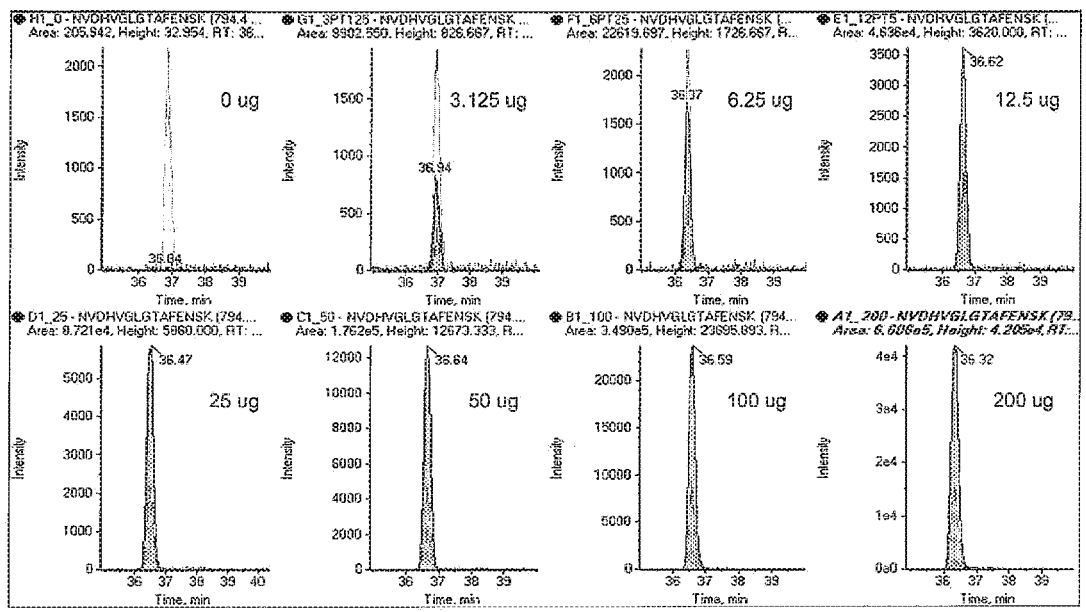
FIG. 1: Mass chromatogram of extracted transitions of peptides from one set of standard curve data. (a) transitions of peptide NVDHVGLGTAFENSK (SEQ ID NO:4). The peak areas for transition 794.4/1023.5 are integrated (cross-hatched). The other three traces are for transitions 794.4/853.4 (pink), 798.4/1031.5 (orange), 798.4/861.4 (green); (b) transitions of peptide VEFWPCSPITQGDR (SEQ ID NO:24), The peak areas for transition 846.9/1131.5 are integrated (cross-hatched). The other three traces are for transitions 846.9/786.4 (pink), 851.9/1141.5 (orange), 851.9/796.5 (green).
Figure 1:
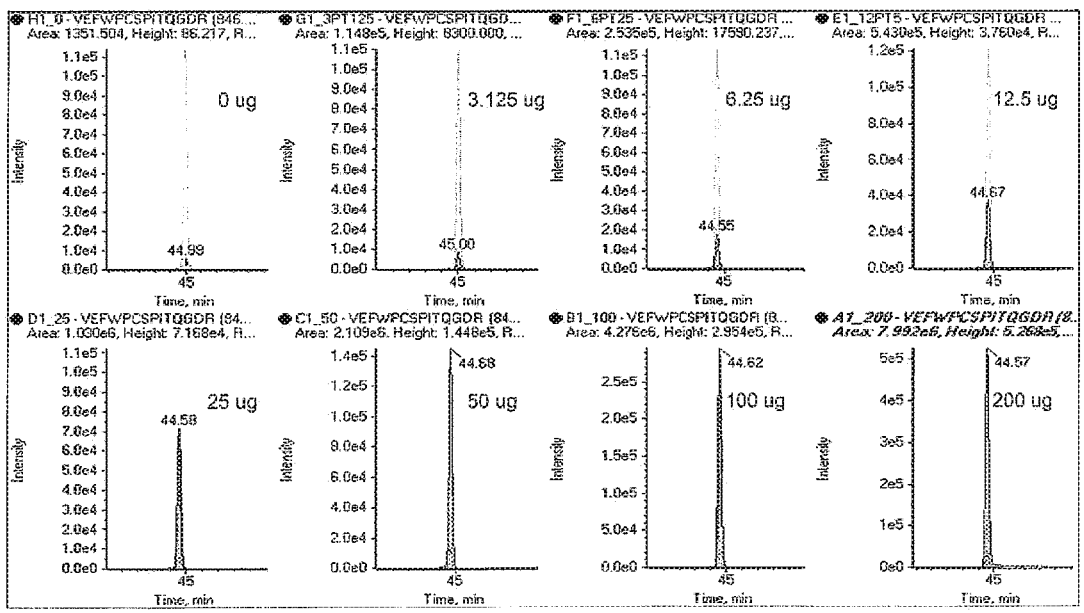

```
Orange box: Common peptide for both PCV2a and 2b:
                                          (SEQ ID NO: 24)
VEFWPCSPITQGDR Pink box: PCV2a-specific peptide:
                                          (SEQ ID NO: 26)
ISIPFEYYR Blue box: PCV2a-specific peptide:
                                          (SEQ ID NO: 4)
NVDHVGLGTAFENSK Green box: PCV2b-specific peptide:
                                          (SEQ ID NO: 27)
SVPFEYYR Purple box: PCV2b-specific peptide:
                                          (SEQ ID NO: 15)
TITQPFSYHSR
```

DETAILED DESCRIPTION OF THE INVENTION

The invention is based on the surprising finding that mass spectroscopic analyses, in particular by using multiple reaction monitoring-mass spectrometry (MRM-MS), are suitable for quantifying the amount of viral proteins, in particular of viral like particles (VLPs) such as VLPs composed of two different viral proteins, in a sufficient way, particularly also in a sample including antibodies binding to said viral proteins and VLPs.

The invention is hence directed to a method of quantifying the presence of a one or more proteins (natural or recombinant) from an infectious agent, such as a virus, bacteria, *mycoplasma*, prion, or parasite, in a sample, comprising
(a) adding a known quantity of at least one stable-isotope-labeled signature peptide specific to at least one infectious agent protein to the sample;
(b) digesting the sample with a protease;
(c) running mass-spectroscopic analyses of the sample; and
(d) determining the amount of infectious agent protein in the sample.

In one aspect, the invention thus relates to a method of quantifying the presence of one or more viral proteins in a sample, comprising:
(a) digesting the sample with a protease;
(b) adding a known quantity of at least one stable-isotope-labeled signature peptide specific to at least one viral protein to the sample;
(c) running mass-spectroscopic analyses of the sample, preferably by using multiple reaction monitoring-mass spectrometry (MRM-MS); and
(d) determining the amount of viral protein in the sample.

Said sample is in particular a sample of a preparation, wherein preferably the preparation is a vaccine preparation. More preferably, said sample is a vaccine preparation sample.

In a particular preferred embodiment, the preparation described herein contains agents which bind to the one or more viral proteins, wherein the agents are preferably antibodies.

Within the context of the present invention, it is in particular understood that the term "mass-spectroscopic" is equivalent to the term "mass-spectrometric".

According to a preferred aspect of the invention, the one or more viral proteins are capable of forming a virus like particle and/or the sample comprises virus like particles composed of a plurality of the one or more viral proteins, wherein said virus like particles are preferably composed of PCV2a ORF2 and/or PCV2b ORF2.

The determining the amount of viral protein in the sample in particular comprises or consists of determining the amount of viral protein in the sample by comparing the results of the sample mass-spectroscopic analysis, wherein preferably in the mass-spectroscopic analysis the signal of the stable-isotope-labeled signature peptide is compared with the signal of one or more peptides produced by the protease digestion of the sample, in particular with the signal of one or more peptides generated by the protease digestion of the one or more viral proteins in the sample.

Preferably, the signature peptides are preselected by determining that they are specific to the protease digest of the viral protein to be quantified and/or that they are specifically absent from the protease digest of the sample in the absence of the viral protein.

According to another preferred aspect, the method of quantifying the presence of one or more viral proteins in a sample of the present invention further comprises determining the amount of viral protein in the sample by comparing the results of the sample mass-spectroscopic analysis with a calibration standard curve; and/or running mass-spectroscopic analyses of standards containing known amounts of labeled and/or unlabeled signature peptides; and determining the amount of viral protein in the sample by comparing the results of the sample mass-spectroscopic analysis with the results of the standards, wherein preferably a calibration standard curve is generated with the results of the standards and compared with the results of the sample mass-spectroscopic analysis.

In another aspect, the invention also relates to a method of making a vaccine preparation containing one or more viral vaccines, comprising using a multiple reaction monitoring-mass spectrometry (MRM-MS) for quantitative and/or qualitative assays for one or more preparation or quality control determinations.

Preferably, the vaccine preparation contains agents, preferably antibodies, which bind to a viral protein in the viral vaccine.

The affinity constant for the binding of the agents to the viral protein, as described herein, is preferably in the range of $10^5$ mol-1 to $10^{12}$ mol-1 or above.

In a preferred aspect, the method of making a vaccine preparation of the present invention preferably comprises the steps of:
(a) adding a known quantity of at least one stable-isotope-labeled signature peptide specific to at least one viral protein to the sample;
(b) digesting the sample with a protease;
(c) running mass-spectroscopic analyses of the sample; and
(d) determining the amount of viral protein in the vaccine preparation.

Preferably, the determining the amount of viral protein in the vaccine preparation comprises or consists of determining the amount of viral protein in the vaccine preparation sample by comparing the results of the sample mass-spectroscopic analysis, wherein preferably in the mass-spectroscopic analysis the signal of the stable-isotope-labeled signature peptide is compared with the signal of one or more peptides produced by the protease digestion of the sample, in particular with the signal of one or more peptides produced by the protease digestion of the one or more viral proteins in the sample.

In another preferred aspect of the method of making a vaccine preparation of the present invention, the signature peptides are preselected by determining that they are specific to the protease digest of the viral protein to be quantified and/or that they are specifically absent from the protease digest of the preparation in the absence of the viral protein.

According to a particular preferred aspect, the method of making a vaccine preparation of the present invention further comprises determining the amount of viral protein in the vaccine preparation sample by comparing the results of the sample mass-spectroscopic analysis with a calibration standard curve; and/or running mass-spectroscopic analyses of standards containing known amounts of labeled and/or unlabeled signature peptides; and determining the amount of viral protein in the vaccine preparation sample by comparing the results of the sample mass-spectroscopic analysis with the results of the standards, wherein preferably a calibration standard curve is generated with the results of the standards and compared with the results of the sample mass-spectroscopic analysis.

According to a particular preferred aspect, the one or more viral proteins, as described herein, is one or more viral capsid proteins, preferably ORF2 of a porcine circovirus (PCV) or VP2 of porcine parvovirus (PPV).

Preferably, the signature peptides, as described herein, are one or more of the following stable-isotope-labeled peptides:

NVDHVGLGTAFENSK, (SEQ ID NO: 4)

TFGYTVK, (SEQ ID NO: 5)

ATTVTTPSWAVDMMR (SEQ ID NO: 6)

FNIDDFVPPGGGTNKISIPFEYYR (SEQ ID NO: 7)

ATALTYDPYVNYSSR (SEQ ID NO: 8)

HTIPQPFSYHSR (SEQ ID NO: 9)

YFTPKPVLDSTIDYFQPNNK (SEQ ID NO: 10)

VTMYVQFR (SEQ ID NO: 11)

MTTVTTPSWNVDMMR, (SEQ ID NO: 12)

FNINDFLPPGGGSNPLTVPFEYYR, (SEQ ID NO: 13)

ANALTYDPYVNYSSR, (SEQ ID NO: 14)

HTITQPFSYHSR, (SEQ ID NO: 15)

YFTPK, (SEQ ID NO: 16)

PVLDR, (SEQ ID NO: 17)

LQTTGNVDHVGLGTAFENSIYDQDYNIR, (SEQ ID NO: 18)

ITMYVQFR, (SEQ ID NO: 19)

EFNLK, (SEQ ID NO: 20)

DPPLNPK, (SEQ ID NO: 21)

YFTPK PVLDR, (SEQ ID NO: 22)

EFNLK DPPLNPK, (SEQ ID NO: 23)

VEFWPCSPITQGDR, (SEQ ID NO: 24)

GVGSTAVILDDNFVTK, (SEQ ID NO: 25)

and any peptide having an amino acid sequence that is at least 80% identical to an amino acid sequence selected from the group consisting of SEQ ID NO: 4 to 25, wherein said peptides are more preferably labeled, in particular at the C-terminal amino acid residue, with at least one stable isotope selected from H2, C13, and N15.

As used herein, it is in particular understood that the term "identical to the sequence of SEQ ID NO: X" is equivalent to the term "identical to the sequence of SEQ ID NO: X over the length of SEQ ID NO: X" or to the term "identical to the sequence of SEQ ID NO: X over the entire length of SEQ ID NO: X", respectively. In this context, "X" is any integer selected from 1 to 28 so that "SEQ ID NO: X" represents any of the SEQ ID NOs mentioned herein.

The protease, as described in the context of the present invention, is preferably selected from the group consisting of trypsin, chymotrypsin, pepsin, thrombin, papain, bromelain, thermolysin, subtilisin, Factor Xa, *Staphylococcus aureus* protease, carboxypeptidase A, and combinations thereof.

Additionally, according to a further aspect of the present invention, the method of quantifying the presence of one or more viral proteins in a sample of the present invention is used for the diagnosis or monitoring of a virus infection, wherein the virus infection is particularly an infection with PCV2, more particular an infection with PCV2a and/or PCV2b, and/or wherein the animal is a pig.

Preferably the sample is in particular a sample of animal material, or a sample of a preparation of animal material, wherein the animal material is preferably selected from body fluid and tissue.

Said animal material is preferably selected from blood, blood serum, blood plasma, urine, colostrum, tissue sections, and tissue biopsies.

The invention preferably provides improved methods and compositions for the quantitative determination of a component, preferably an antigen, in a vaccine, preferably a combination vaccine, in particular wherein another component in the vaccine interferes with standard immunoassays. In particular, the invention relates to the quantitative determination of a first vaccine antigen in a combination vaccine with a second vaccine, which second vaccine includes a biological component, e.g., serum, which interferes with the standard immunoassay. For example, the serum may be derived from animals which have been exposed to the first antigen, whereby the serum contains antibodies which interfere with an ELISA assay for the first antigen. For example, both *Mycoplasma hyopneumoniae* (*M. hyo.*) and porcine circovirus 2 (PCV2) are pathogenic to swine, and vaccinating against both pathogens is desirable. The medium used to grow *M. hyo.* includes porcine serum. Because most swine are immunized against PCV2, the medium used to grow *M. hyo.* includes variable amounts of anti-PCV2 antibodies. These anti-PCV2 antibodies can interfere with a standard immunoassay that is used to either quantify or monitor stability of a combination vaccine that includes both therapeutic amounts of PCV2 antigen and *M. hyo.* antigen after the antigens are combined together.

Multiple Reaction Monitoring-Mass Spectrometry

Multiple reaction monitoring-mass spectrometry (MRM-MS, or MRM as used herein), combined with a stable isotope-labeled internal standard, is used in the pharmaceutical industry for the quantitative detection of small molecules. MRM-MS is theoretically useful when no suitable specific antibody-pairs are available. MRM-MS is also theoretically suitable when a multiplex panel is needed or the candidate protein is a modified protein, and can measure protein in either high or low concentrations from a variety of sources including serum and tissue. MRM-MS can also measure multiple target proteins simultaneously in one assay. Optionally, stable heavy isotope-labeled peptides are commonly used as internal standards. Thus, despite the uncertainties involved in identifying and making suitable reference peptides, MRM-MS has the potential to be used in potency assays for vaccines during manufacture and after final processing, to be useful for vaccine stability testing, for reference stability testing (i.e., demonstration of stability), and the identification of new disease biomarkers. Despite the uncertainties inherent in the technology, in certain applications MRM-MS theoretically could be used to address certain problems presented by ELISA detection. The chart below generally summarizes a comparison of the two techniques.

Comparison of ELISA and MRM-MS Methods for Quantification of a Biotherapeutic

| ELISA | MRM-MS |
|---|---|
| Requires specific antibody pairs | Non-antibody based assay |
| CV <20% | CV <10% |
| Antibody can be cross-reactive | protein sequence specific |
| Sensitivity: ng/mL | Same |

-continued

| ELISA | MRM-MS |
|---|---|
| Matrix: serum or plasma | Same |
| Only one protein can be measured per assay | 1-50 target proteins can be measured simultaneously in a single analysis |
| The ELISA assay running time: 4–8 hr | Comparable |

When MRM was initially developed, it was not practical for protein quantification in complex biological samples because MRM assays need defined proteins for potency assays and reference stability monitoring. This issue has been overcome in a few specific cases, where MRM has been demonstrated to simultaneously and absolutely quantify hemagglutinin antigens (HAs) of three influenza subtypes in commercial vaccines. See Williams et al. 2008, Quantification of influenza virus hemagglutinins in complex mixtures using isotope dilution tandem mass spectrometry. Vaccines 26: 2510-2520. Williams et al. showed that the total HA amounts of H1, H3 and B were quantified to be 24, 16 and 38 micrograms per 0.5 ml by using MRM methods in commercial vaccines. However, the influenza vaccine is comprised of partially-purified antigen, does not contain any adjuvant, and the hemagglutinin is not suspended in a complex matrix, Thus, while MRM may be able to quantitate specific components of highly complex biotherapeutics if suitable targets can be identified, many targets are unsuitable for MRM detection due to various molecular interactions, e.g., those containing certain adjuvants, and those in which the antigen is in a complex matrix of competing antibodies and/or a proteinaceous milieu that could affect quantitation.

There are many applications in vaccine production and quality control analysis for which MRM may be useful, in particular wherein the standard ELISA testing is not possible, as discussed above. In particular, ELISA cannot be used where other components of the complex mixture of the vaccines and other components are found, including, e.g., polyvalent vaccines wherein multiple components have similar antigenic properties, or vaccines which include serum from animals that may have interfering antibodies as a result of prior infection or vaccination. In these cases, specific peptides may be identified which can be used as "signature peptides" to detect and quantify the amount and nature, e.g., intact or degraded, antigen in the mixture.

For example, porcine circovirus type 2 (PCV2) has been indicated as the causative agent in porcine multisystemic wasting syndrome (PMWS). Open reading frame number 2 (ORF2) encodes for a nucleocapsid protein that has been reported as immunogenic. ORF2 has been cloned into a baculovirus expression system and is capable of being expressed when grown in insect cell culture. See for example, U.S. Pat. Nos. 7,910,306; 7,914,992; and 8,025,888. Purified ORF2 protein or ORF2 prepared in a monovalent vaccine matrix can be tested by MRM directly; however, even more particularly, when it is present ORF2 protein antigen is one component of a bivalent vaccine formulation, the other component consists of another antigen such as *Mycoplasma hyopneumoniae* that is produced in a media containing porcine serum. A combination vaccine thus contains in the vaccine matrix varying amounts of endogenous porcine serum IgG antibodies (PAb), which naturally compete with the ELISA antibodies in binding to the ORF2-antigen, which in turn interferes with ELISA assays. These vaccine preparations can be tested either directly as the vaccine formulation, or extracted from the formulation matrix using an immunoprecipitation (IP) approach or size exclusion chromatography (SEC) purification technique.

Thus multiple approaches exist for use of signature peptides in detecting and quantitating vaccine proteins using MRM. These different approaches include:

a. Multiple Reaction Monitoring (MRM) for Quantitation of, e.g., PCV2 ORF2, Using a Single Peptide This method directly quantifies the amount of a protein target without requiring the use of antibodies (Abs).

Although some proteins can be directly quantitatively analyzed using LC-MS/MS, (i.e., MRM-MS) technology, others proteins, such as PCV2 ORF2, are too large for direct quantitative analysis. Therefore, such proteins can be consecutively treated in a variety of ways to prepare smaller peptides for MRM analysis.

In what follows, a general procedure is discussed for the preparation of a sample for PCV2 ORF2, which comprises the following general steps: denaturation, reduction, alkylation and trypsinization. However, one of skill in the art will appreciate that variations on these preparative steps can be routinely performed, in particular using different enzymes to cleave the protein. A typical proteolytic enzyme, trypsin, is discussed with respect to the general procedure for performing MRM to quantify the amount of protein in a complex sample such as a vaccine matrix.

Trypsin cuts at peptide bonds of polypeptide chains specifically following either an arginine (R) or a lysine (K) and generates a global tryptic peptide pool. Distinct characteristic tryptic peptides are selected that fulfill the following criteria:

a. A. peptides with unique amino acid sequences specific of the PCV2 ORF2 protein from which they had been cleaved;

b. the amount of these peptides corresponds stoichiometrically to the amount of whole PCV2 ORF2 protein from which they had been cleaved;

c. such peptides are ionized well by positive electrospray ionization (ESI).

The thus-produced peptides are referred to as endogenous "signature" peptides.

MRM additionally utilizes isotopically labeled synthetic peptide homologs (i.e., exogenous "signature" peptides) as internal standards to quantitate the abundance of endogenous signature peptides. Protein amounts are determined by comparing the amount of an endogenous signature peptide to a known amount of a corresponding exogenous signature homolog (i.e., isotopically labeled synthetic peptides homolog). The heavy label on the synthetic homolog causes a shift in the mass spectrum in MRM, which allows for straightforward comparison to the endogenous signature peptide.

After tryptic digestion of the sample, known amounts of exogenous "signature" peptides are added to the digestion assay. As analysis of complex peptide mixtures can be simplified by additional stages of separation prior to mass spectrometry, the peptide mixture is first subjected to reversed-phase high performance liquid chromatography (HPLC) and peptides are stratified based upon their hydrophobicity. The purpose of the liquid chromatography step is to spread out the delivery of peptides to the electrospray element over a long period of time to increase the number of peptides that can be identified.

Subsequently, both eluted analyte species, i.e., endogenous and exogenous signature peptides are continually on-line analyzed based on quantitation by triple quadrupole mass spectrometry with a tandem quadrupole instrument operated in the MRM mode:

The peptides are delivered to the mass spectrometer at low pH (e.g., in formic acid) to convert them to cationic form. Peptides are individually ionized in the source region using ESI and resulting in charged analyte ions. As the peptide ions are delivered to the mass spectrometer, the first stage displays an ever-changing readout of m/z (mass-to-change ratio) of the various tryptic peptides (the MS1 spectrum). The peak heights (currents) are functions of the abundances of the individual peptide ions but are influenced by other physicochemical properties. The m/z information in the MS1 spectra is generally not sufficient to identify specific peptides.

To accomplish this task, selected peptides undergo another level of analysis initiated by targeted fragmentation of the selected "parent" peptide ion.

The most commonly used method for peptide fragmentation is collision-induced dissociation (CID), which generally breaks a single peptide bond, fragmenting each peptide ion into two pieces. The specific peptide bond broken in a given parent peptide ion is variable, however, yielding a host of fragments. Thus, CID creates complementary b- and y-type ions series of fragments. The b-ions contain the NH2 terminus through the cleavage site; the y-ions contain the COOH terminus through the cleavage site.

The mass spectrometer displays the so-called "fragmentation spectrum" (MS2 spectrum; bottom). Here, the difference in m/z between adjacent b- or y-series peaks is exactly the residue mass of the amino acid present in one fragment, but absent in the other. Thus, in the difference between the y1-10 peak (m/z=1,276.4) and the y1-9 peak (m/z=1,147.4) is exactly the residue mass of a glutamic acid (E; 129.0 Da).

In theory, the peptide sequence could be read directly from the MS2 spectrum. In practice, however, a computer uses the MS2 spectrum together with the m/z of the parent peptide ion to compare with all of the theoretical spectra from the appropriate protein species to identify the tryptic peptide and the protein of origin. The database of theoretical peptide spectra is generated from in silico tryptic digestion of all of the amino acid sequences derived from the appropriate single-species protein sequencing database.

For example, porcine circovirus 2 (PCV2) open reading frame 2 (ORF2) has the amino acid sequence:

(SEQ ID NO: 1)

MTYPRRRYRRRRHRPRSHLGQILRRRPWLVHPRHRYRWRRKNGIFNTRLS

RTFGYTVKATTVTTPSWAVDMMRFNIDDFVPPGGGTNKISIPFEYYRIRK

VKVEFWPCSPITQGDRGVGSTAVILDDNFVTKATALTYDPYVNYSSRHT

IPQPFSYHSRYFTPKPVLDSTIDYFQPNNKRNQLWLRLQTSRNVDHVGL

GTAFENSKYDQDYNIRVTMYVQFREFNLKDPPLEP within which the unique tryptic peptide VEFWPCSPITQGDR (underline above; SEQ ID NO:24) has a stronger signal than other peptides from PCV2 ORF2 and is considered a "signature peptide" for PCV2 ORF2. This peptide can be labeled with a heavy isotope, e.g., $^{13}C$ and/or $^{15}N$. A known quantity of the labeled signature peptide can be used to spike a trypsin digest sample of PCV2 (e.g., INGELVAC CIRCOFLEX® (inactivated baculo-expressed PCV2 ORF2 vaccine)). Multiple reaction monitoring MS (MRM-MS) is then run with the spiked sample using standard protocols (see below).

In the first quadrupole (Q1), the signature peptide is selected to pass. Subsequently, the signature peptide is fragmented from the PCV2 protein in the second quadrupole (Q2). Only the selected fragments that are generated in Q2 are analyzed in the third quadrupole (Q3). The results allow the quantification of the ratio of the unlabeled or "light" signature peptide to the labeled or "heavy" signature peptide. This analysis can be repeated with multiple quantities of known amounts of labeled peptides with an unknown to generate a standard curve for absolute quantification. By using the ratio of the heavy to light signature peptide, the amount of PCV2 protein present in the initial sample can be calculated.

Data show that there is no interference from the background in the monitored MRM channel. MRM can quantitate PCV2 ORF2 based on the quantitation of proteolytic peptides as surrogates for the corresponding intact ORF2.

b. Quantitation of, e.g., Intact PCV2 ORF2 VLPs with Multiple Signature Peptides Using MRM, multiple signature peptides can be used to directly quantitate PCV2 ORF2 protein in the fixed combination vaccine to ensure the PCV2 ORF2 protein is intact. If the signal was decreased from one of the signature peptides, then the full length ORF2 is degraded. Signature peptides are underlined in the ORF2 sequence below.

```
                                              (SEQ ID NO: 1)
MTYPRRRYRRRRHRPRSHLGQILRRRPWLVHPRHRYRWRRKNGIFNTRLS

RTFGYTVKATTVTTPSWAVDMMRFNIDDFVPPGGGTNKISIPFEYYRIRK

VKVEFWPCSPITQGDRGVGSTAVILDDNFVTKATALTYDPYVNYSSRHT

IPQPFSYHSRYFTPKPVLDSTIDYFQPNNKRNQLWLRLQTSRNVDHVGL

GTAFENSKYDQDYNIRVTMYVQFREFNLKDPPLEP
```

For example, three of the characteristic or signature tryptic peptides can be used for monitoring in the assay: one as the primary peptide for quantitation and two others as secondary peptides for qualitative confirmation. For PCV2, the peptide sequences are, for example, as follows:

```
          Primary peptide:
                                      (SEQ ID NO: 24)
          VEFWPCSPITQGDR Secondary peptide 1:
                                      (SEQ ID NO: 26)
          ISIPFEYYR Secondary peptide 2:
                                      (SEQ ID NO: 4)
          NVDHVGLGTAFENSK
```

The assay also incorporates stable isotope-labeled internal standards (ISs), which are signature peptides, for all three of the target peptides and the associated analyte/IS response ratios are used in the analysis. The internal standard/signature peptide sequences are as follows:

```
    Primary I.S. used for quantitation:
                                      (SEQ ID NO: 24)
    ORF2 (P1*) (VEFWPCSPITQGDR (+10 Da))
```

```
    Secondary I.S. used qualitatively:
                                      (SEQ ID NO: 26)
    ORF2 (P2*) (ISIPFEYYR (+10 Da))

Secondary I.S. used qualitatively:
                                      (SEQ ID NO: 4)
    ORF2 (P3*) (NVDHVGLGTAFENSK (+8 Da))
```

The PCV2 ORF2 VLPs can be extracted from the vaccine samples by size-exclusion chromatography and then MRM can be used to absolutely quantify the VLPs if desired.

c. Quantitation and Differentiation of Antigenically Similar VLPs, e.g., PCV2a and PCV2b, Using IP-MRM PCV2a and PCV2b are antigenic subtypes of antigenically similar, but not identical non-enveloped VLPs. Similarly, the PCV2a ORF2 and PCV2b ORF2 VLP subtypes are antigenically similar, but are not identical at the amino acid level. The desired PCV2 ORF2 vaccine will contain a mixture of VLPs comprised of both PCV2a ORF2 and PCV2b ORF2 subtypes.

Typically, an ELISA method would be used to determine the relative antigen content (RAC) or relative potency (RP) of the two different PCV2 ORF2 subtypes in a vaccine. However, an ELISA capable of differentiating the inclusion levels of PCV2a and PCV2b would require two different MAb (one MAb that reacts only to PCV2a, and the other MAb reacting only to PCV2b). But, the generation of two distinct MAbs that are able to differentiate between the two antigenically similar PCV2a and PCV2b VLP would be a very difficult, possibly impossible, task.

IP-MRM allows the use of polyclonal antibodies to bind both PCV2a and PCV2b, followed by the subsequent differentiation and quantitation of the amounts of PCV2a and PCV2b by MRM.

In the IP approach, polyclonal anti-ORF2 antibodies are added to the vaccine sample, allowed to bind to the ORF2, and the resulting ORF2-Pab complexes are captured on magnetic beads coated with Protein G. As ORF2 is too large for practical direct quantitative analysis using LC-MS/MS technology, the bound proteins are subjected to "onbead" proteolysis with trypsin, following standard protein denaturation, reduction, and alkylation processing steps. The characteristic peptide fragments produced by this procedure can then be quantified as surrogates of the ORF2 protein by LC-MS/MS (liquid chromatograph multiple reaction monitoring mass spectrometry, or MRM) with the required sensitivity, specificity, and precision and accuracy.

d. Quantitation of, e.g., PCV2 ORF2 VLPs by Immunoaffinity (IP)-MRM

IP-MRM incorporates the use of a polyclonal antiserum or a specific monoclonal antibody (MAb) directed against a virus-like particle (VLP), core-like particle (CLP), or an immunologically relevant protein/peptide. This method is useful for quantitation and/or relative potency (RP) determination of the inclusion levels of VLPs, CLPs, and immunologically relevant proteins in vaccines. This method uses a combination of ELISA with MRM. For example, using standard techniques, biotinylated anti-PCV2 ORF2 monoclonal Ab is attached to streptavidin coated ELISA plates. The Abs are blocked then PCV2 ORF2 from a vaccine, e.g., INGELVAC CIRCOFLEX® (inactivated baculo-expressed PCV2 ORf2 vaccine) or INGELVAC MYCOFLEX® (inactivated *Mycoplasma hyopneumoniae* bacterin vaccine), which comprises antigens respectively against PCV2 and *M. hyo*, is loaded and allow to bind on the plates. Using standard techniques, the ORF2 VLPs are then released from the plate and injected into a LC-MRM and quantified.

e. Quantitation of, e.g., PCV2 ORF2 VLPs by Size Exclusion Chromatography (SEC)-MRM Similarly to the IP-MRM procedure, but not relying on the use of antibodies, the use of SEC as a pre-step ensures that only VLP or inner CLP is present in a sample to be measured, as only an intact VLP or CLP structure will pass through into the void fraction. SEC-MRM allows the separation of VLP from a complex matrix with high levels of non-relevant, extraneous proteins. This method is antibody-free. If there is the possibility of a batch of antigen to contain both intact VLP and degraded VLP, the addition of the SEC step ensures that only intact VLP (i.e., true VLP) will be measured in the MRM portion of the assay.

In the above applications, specific reference was made to identification of the ORF2 of PCV2. However, the methods of the invention can also be applied to detection and quantitation of other vaccines, including non-analogous proteins of those vaccines, including but not limited to:

f. Quantitation of Non-Enveloped, Monomeric PPV VP2 VLP with IP-MRM

Porcine parvovirus (PPV) VP2 VLP can be quantitated as above, for quantitation of the amount of antigenic subtypes of antigenically similar, but not identical VLP (i.e., quantitative differentiation of NADL PPV VLP from IDT27, another PPV VLP) in a vaccine containing both antigens. In the IP approach, monoclonal or polyclonal anti-PPV antibodies are added to the vaccine sample, allowed to bind to the PPV VP2 VLP, and the resulting PPV VP2 VLP-antibody complexes are captured on magnetic beads coated with Protein G. As PPV VP2 VLP is too large for practical direct quantitative analysis using LC-MS/MS technology, the bound proteins are subjected to "onbead" proteolysis with trypsin, following standard protein denaturation, reduction, and alkylation processing steps.

g. Quantitation of Non-Enveloped, Dimeric VLPs with IP-MRM

Feline Calicivirus (FCV) VLP (comprised of VP1 and VP2)—as above, quantitation of the amount of antigenic subtypes of antigenically similar, but not identical VLP (i.e., quantitative differentiation of FCV DD1 from IFCV 666). In the IP approach, monoclonal or polyclonal anti-FCV antibodies are added to the vaccine sample, allowed to bind to the FCV VLP, and the resulting FCV VLP-antibody complexes are captured on magnetic beads coated with Protein G. As FCV VLP is too large for practical direct quantitative analysis using LC-MS/MS technology, the bound proteins are subjected to "onbead" proteolysis with trypsin, following standard protein denaturation, reduction, and alkylation processing steps.

Norovirus vaccine—quantitation of VLP of multiple subtypes of antigenically similar, but not identical VLP mixture in a vaccine. In the IP approach, monoclonal or polyclonal anti-Norovirus antibodies are added to the vaccine sample, allowed to bind to the Norovirus VLP, and the resulting Norovirus VLP-antibody complexes are captured on magnetic beads coated with Protein G. As Norovirus VLP is too large for practical direct quantitative analysis using LC-MS/MS technology, the bound proteins are subjected to "onbead" proteolysis with trypsin, following standard protein denaturation, reduction, and alkylation processing steps.

Rotavirus vaccine—quantitation of VLP of multiple subtypes of antigenically similar, but not identical VLP mixture in a vaccine. In the IP approach, monoclonal or polyclonal anti-Rotavirus antibodies are added to the vaccine sample, allowed to bind to the Rotavirus VLP, and the resulting Rotavirus VLP-antibody complexes are captured on magnetic beads coated with Protein G. As Rotavirus VLP is too large for practical direct quantitative analysis using LC-MS/MS technology, the bound proteins are subjected to "onbead" proteolysis with trypsin, following standard protein denaturation, reduction, and alkylation processing steps.

h. Quantitation of Non-Enveloped, Multimeric VLP with IP-MRM or SEC-MRM

A Bluetongue virus (BTV) VLP is comprised of an inner core like particle (CLP) made of VP3 and VP7, and an outer capsid of VP2 and VP5. Importantly, CLP do not induce neutralizing antibodies in a vaccinated animal. Intact VLP is the preferred form of antigen, as neutralizing antibodies are directed to VP2 and VP5 that comprise the outer layer of the VLP. There are at least 24 serotypes of BTV distributed throughout the world, and the optimal BTV VLP vaccine would contain VLPs of many different serotypes.

SEC-MRM or IP-MRM may be used for the quantitative differentiation of antigen levels in multivalent vaccine having a mixture of many BTV VLPs. SEC would collect both CLP and VLP in the void fraction. However, MRM may be used measure the exact quantities of VP3, VP7, VP2, and VP5 in the void fraction, and the ratios of VP3, VP7, VP2, and VP5 may be used to determine the percentage of CLP and VLP present in the sample. Such differentiation would be necessary to comply with regulatory needs and to assure proper dosages (i.e., relative potency) in a commercial product.

i. Quantitation of Non-Enveloped, HepB Core Particles with IP-MRM

The nucleoprotein of the hepatitis B virus (HBV) exists in two structural forms. The nucleocapsid, designated the hepatitis core antigen (HBcAg), is a protein that self-assembles into particles that encapsidate the viral genome and polymerase and is essential to the function and maturation of the virion. A secreted, nonparticulate second form of the nucleoprotein is designated the precore or hepatitis B e antigen (HBeAg). The HBcAg and HBeAg are distinctly recognized by antibodies but, due to their extensive amino acid homology, are highly cross-reactive at the T-cell level.

HepB split core (HepBsc) particles can be used to display immunogenic/-immunomodulating proteins or peptides on the surface of the HepBsc. SEC-MRM or IP-MRM may be used to quantitate both the quantity and/or ratio of HepBsc particles and its displayed target present in a vaccine.

j. Quantitation of Non-Enveloped, PCV2 ORF2 VLP Carrier Protein with IP-MRM

PCV2 ORF2 VLP particles can be used as a carrier of immunogenic/immunomodulating proteins or peptides. SEC-MRM or IP-MRM could be used to quantitate both the quantity and/or ratio of PCV2 ORF2 VLP and its displayed target present in a vaccine.

k. Quantitation of Influenza M-Based, Enveloped VLP with IP-MRM

The Matrix (M) protein of influenza can form enveloped VLP structures. Immunologically relevant antigens such hemagglutinin (HA) and neuraminidase (N) can be anchored in the envelope of the VLP by their native transmembrane domain. Preferably, any influenza VLP-based vaccine would contain several HA and N proteins (e.g., H1 or H3 and N1 or N2; similar to that found in the annual human influenza vaccines). M-based VLP are not limited to carrying only influenza antigens, as these VLP can incorporate transmembrane domain-anchored proteins from other viruses (e.g., rabies G glycoprotein). SEC-MRM or IP-MRM could be used to quantitate the amount of the viral protein antigen.

l. Quantitation of Baculovirus-Displayed Antigen VLPs with IP-MRM

Immunologically relevant antigens such hemagglutinin (HA), neuraminidase (N), or rabies G can be anchored in the baculovirus envelope by their native transmembrane domain. Such a recombinant baculovirus could be the basis of a therapeutic vaccine.

SEC-MRM or IP-MRM may be used to quantitate the displayed target present in a vaccine. Also, SEC-MRM or IP-MRM may be used to quantitate both the quantity and/or ratio of the baculovirus-associated gp64 (the major baculovirus envelope protein) and its displayed target present in a vaccine.

m. Quantitation of Retroviral Gag-Based, Enveloped VLP with IP-MRM

The gag protein of retroviruses can form enveloped VLP structures.

Immunologically relevant antigens such hemagglutinin (HA), neuraminidase (N), or rabies G can be anchored in the baculovirus envelope by their native transmembrane domain. SEC-MRM or IP-MRM may be used to quantitate the amount of the viral protein antigen.

n. Combinations of MRM with Additional Steps, e.g., Pre-Purification and/or Simultaneous Detection of Additional Proteins In addition to detection of the PCV2 ORF2 of SEQ ID NO:1, the method of the invention can be used to detect and quantitate subtypes of said virus, e.g., in a polyvalent vaccine. PCV2a and PCV2b are antigenic subtypes of antigenically similar, but not identical VLPs. Similarly, the PCV2a ORF2 and PCV2b ORF2 VLP subtypes are antigenically similar, but are not identical at the amino acid level. The desired PCV2 ORF2 vaccine will contain a mixture of VLPs comprised of both PCV2a ORF2 and PCV2b ORF2 subtypes.

Typically, an ELISA method would be used to determine the relative antigen content (RAC) or relative potency (RP) of the two different PCV2 ORF2 subtypes in a vaccine. However, an ELISA capable of differentiating the inclusion levels of PCV2a and PCV2b would require two different MAb (one Mab that reacts only to PCV2a, and the other Mab reacting only to PCV2b). But, the generation of two distinct Mabs that are able to differentiate between the two antigenically similar PCV2a and PCV2b VLP would be a very difficult, possibly impossible, task.

IP-MRM allows the use of polyclonal antibodies to bind both PCV2a and PCV2b, followed by the subsequent differentiation and quantitation of the amounts of PCV2a and PCV2b by MRM.

SEQ ID NO:1 is the amino acid sequence of the full-length ORF2 of the most common subtype of PCV2, also known as PCV subtype PCV2a:

1 MTYPRRRYRRRRHRPRSHLGQILRRRPWLVHPRHRYRWRRKNGIFN TRLS

51 RTFGYTVKATTVTTPSWAVDMMRFNIDDFVPPGGGTNKISIPFEYY RIRK

101 VKVEFWPCSPITQGDRGVGSTAVILDDNFVTKATALTYDPYVNYSS RHTI

151 PQPFSYHSRYFTPKPVLDSTIDYFQPNNKRNQLWLRLQTSRNVDHV GLGT

201 AFENSKYDQDYNIRVTMYVQFREFNLKDPPLEP

SEQ ID NO:2 and SEQ ID NO:3 are variants of the amino acid sequence of ORF2 of PCV2b:

(SEQ ID NO: 2)

1 MTYPRRRYRRRRHRPRSHLGQILRRRPWLVHPRHRYRWRRKNGIFN TRLS

51 RTFGYTIKRTTVRTPSWAVDMMRFNINDFLPPGGGSNPRSVPFEYY RIRK

101 VKVEFWPCSPITQGDRGVGSSAVILDDNFVPKATALTYDPYVNYSS RHTI

151 TOPFSYHSRYFTPKPVLDGTIDYFQPNNKRNQLWLRLQTAGNVDHV GLGT

201 AFENSIYDQEYNIRVTMYVQFREFNLKDPPLNP;

and (SEQ ID NO: 3)

MTYPRRRFRRRRHRPRSHLGQILRRRPWLVHPRHRYRWRRKNGIFNT

RLSRTIGYTVKKTTVTTPSWNVDMMRFNINDFLPPGGGSNPLTVPFEYY

RIRKVKVEFWPCSPITQGDRGVGSTAVILDDNFVTKANALTYDPYVNYSS

RHTITQPFSYHSRYFTPKPVLDRTIDYFQPNNKRNQLWLRLQTTGNVDHV

GLGTAFENSIYDQDYNIRITMYVQFREFNLKDPPLNPK.

Bold/underlined sequences are "signature peptides" for the respective proteins.

o. Identification of Signature Peptides for MRM Identification

The methods of the invention depend on being able to identify sequences within the protein target in a mixture of other components which are specific for a particular protein in the mixture.

In one embodiment, the sequence of the protein target is analyzed with software that determines the sequences of peptides that are produced with a variety of enzymes. Preferably, those peptides are unique to the desired protein to be detected as compared to the composition in which the desired protein is present, and the peptides are not too small or large to be unsuitable to be used as signature peptides.

Despite this general guidance in selecting signature peptides suitable for use in the invention, confirmation of the utility of signature peptides requires experimental confirmation. For example, two of the three tryptic peptides initially suggested by ABI MultiQuant Software (version 1.0) to be the most likely to be useful in the invention performed as expected. Surprisingly, although peptide ISIPFEYYR (SEQ ID NO:26) had the strongest signal among the three peptides chosen to quantitate the ORF2 protein concentration in initial experiments, this peptide failed to have the required characteristics for quantitative analysis, perhaps due to unexpected interference with a porcine serum protein.

p. Preparation of Samples for MRM Identification

A variety of sample preparation techniques can be used, if necessary, to purify samples prior to MRM analysis, in order to enhance signal quality. These techniques include, for example, immunoaffinity, immunoprecipitation, and size exclusion chromatography.

Definitions

Unless defined otherwise, all technical and scientific terms used herein have the same meaning as is commonly understood by one of skill in the art to which this invention belongs at the time of filing. The meaning and scope of terms should be clear; however, in the event of any latent ambiguity, definitions provided herein take precedent over any dictionary or extrinsic definition. Further, unless otherwise required by context, singular terms shall include pluralities and plural terms shall include the singular. Herein, the use of "or" means "and/or" unless stated otherwise. Furthermore, the use of the term "including", as well as other forms such as "includes" and "included" is not limiting.

"Protein" refers to any protein without limitation and preferably includes those comprised of at least more than 50 amino acids.

"Peptide" refers to shorter polypeptides and preferably includes those comprising 50 or less amino acids, for example between 4 and 50 amino acids, or between 10 and 24 amino acids.

"Analyte protein" and "analyte peptide" refers to the specific protein or peptide to be quantified.

"Signature peptide" includes both an endogenous signature peptide prepared from the analyte protein or peptide by fragmentation by proteases or chemical cleavage, and an exogenous or synthetic peptide that contains an amino acid sequence which corresponds to a sequence in a known or predicted protein to be analyzed and which is labeled in such a manner that the exogenous signature peptide is identical or almost identical to the endogenous peptide generated from the protein(s) to be analyzed, upon fragmentation by proteases or chemicals, except for a slightly different molecular mass. The chemical modification of the mass-labeled peptide internal standard is preferably an incorporation of a stable isotope. In this case, the exogenous signature peptide and the endogenous signature peptide fragmented from the analyte protein will be identical except for a slightly different molecular mass.

"Vaccine" refers to an immunogenic composition that, when administered to an animal, elicits, or is able to elicit—directly or indirectly—an effective immune response in the animal against an antigen in the composition, e.g., an antigen which will elicit an immune response to a pathogenic organism. Preferably, such immune response reduces the incidence of or severity of one or more clinical signs associated with or caused by the infection with one or more pathogenic organisms.

"Antigen" refers to a polypeptide or protein that elicits an immune response as described herein. An "immunogenic" protein or polypeptide includes the full-length sequence of any of the proteins or polypeptides identified herein or analogs or immunogenic fragments thereof. The term "immunogenic fragment" or "immunogenic portion" refers to a fragment or truncated and/or substituted form of an antigen or immunogenic protein or polypeptide that includes one or more epitopes and thus elicits the immunological response described herein. In general, such truncated and/or substituted forms, or fragments will comprise at least six contiguous amino acids from the full-length protein. More preferably, the truncated or substituted forms, or fragments will have at least 10, more preferably at least 15, and still more preferably at least 19 contiguous amino acids from the full-length protein.

An "immune response" or "immunological response" means, but is not limited to, the development of a cellular and/or antibody-mediated immune response to the composition or vaccine of interest. Usually, an immune or immunological response includes, but is not limited to, one or more of the following effects: the production or activation of antibodies, B cells, helper T cells, suppressor T cells, and/or cytotoxic T cells, directed specifically to an antigen or antigens included in the composition or vaccine of interest. Preferably, the host will display either a therapeutic or a protective immunological (memory) response such that resistance to new infection will be enhanced and/or the clinical severity of the disease reduced. Such protection will be demonstrated by either a reduction in number of symptoms, severity of symptoms, or the lack of one or more of the symptoms associated with the infection of the pathogen, a delay in the of onset of viremia, reduced viral persistence, a reduction in the overall viral load and/or a reduction of viral excretion.

"A pharmaceutical- or veterinary-acceptable carrier" refers to any and all solvents, dispersion media, coatings, adjuvants, stabilizing agents, diluents, preservatives, antibacterial and antifungal agents, isotonic agents, adsorption delaying agents, and the like. In some preferred embodiments, and especially those that include lyophilized immunogenic compositions, stabilizing agents for use in the present invention include stabilizers for lyophilization or freeze-drying.

"Adjuvants" as used herein, can include aluminum hydroxide and aluminum phosphate, saponins e.g., QUIL A® (saponin adjuvant), QS-21® (saponin adjuvant; Cambridge Biotech Inc., Cambridge Mass.), GPI-0100® (saponin adjuvant; Galenica Pharmaceuticals, Inc., Birmingham, Ala.), water-in-oil emulsion, oil-in-water emulsion, water-in-oil-in-water emulsion. The emulsion can be based in particular on light liquid paraffin oil (European Pharmacopea type); isoprenoid oil such as squalene or squalane; oil resulting from the oligomerization of alkenes, in particular of isobutene or decene; esters of acids or of alcohols containing a linear alkyl group, more particularly plant oils, ethyl oleate, propylene glycol di-(caprylate/caprate), glyceryl tri-(caprylate/caprate) or propylene glycol dioleate; esters of branched fatty acids or alcohols, in particular isostearic acid esters. The oil is used in combination with emulsifiers to form the emulsion. The emulsifiers are preferably nonionic surfactants, in particular esters of sorbitan, of mannide (e.g. anhydromannitol oleate), of glycol, of polyglycerol, of propylene glycol and of oleic, isostearic, ricinoleic or hydroxystearic acid, which are optionally ethoxylated, and polyoxypropylene-polyoxyethylene copolymer blocks, in particular the Pluronic products, especially L121® (block copolymer surfactant). See Hunter et al., The Theory and Practical Application of Adjuvants (Ed.Stewart-Tull, D. E. S.), John Wiley and Sons, NY, pp 51-94 (1995) and Todd et al., Vaccine 15:564-570 (1997). Exemplary adjuvants are the SPT® emulsion (squalene, TWEEN 80® (polyoxyethylene (20) sorbitan monooleate), and L121® (block copolymer surfactant)) described on page 147 of "Vaccine Design, The Subunit and Adjuvant Approach" edited by M. Powell and M. Newman, Plenum Press, 1995, and the emulsion MF59® (squalene-based adjuvant) described on page 183 of this same book.

A further instance of an adjuvant is a compound chosen from the polymers of acrylic or methacrylic acid and the copolymers of maleic anhydride and alkenyl derivative. Advantageous adjuvant compounds are the polymers of acrylic or methacrylic acid which are cross-linked, especially with polyalkenyl ethers of sugars or polyalcohols. These compounds are known by the term carbomer (Pharmeuropa Vol. 8, No. 2, June 1996). Persons skilled in the art can also refer to U.S. Pat. No. 2,909,462 which describes such acrylic polymers cross-linked with a polyhydroxylated compound having at least 3 hydroxyl groups, preferably not more than 8, the hydrogen atoms of at least three hydroxyls being replaced by unsaturated aliphatic radicals having at least 2 carbon atoms. The preferred radicals are those containing from 2 to 4 carbon atoms, e.g.

vinyls, allyls and other ethylenically unsaturated groups. The unsaturated radicals may themselves contain other substituents, such as methyl. The products sold under the name CARBOPOL® (high molecular weight homo- and copolymers of acrylic acid crosslinked with a polyalkenyl polyether; BF Goodrich, Ohio, USA) are particularly appropriate. They are cross-linked with anallyl sucrose or with allyl pentaerythritol. Among then, there may be mentioned CARBOPOL 974P® (cross-linked polyacrylate polymer), CARBOPOL 934P® (cross-linked polyacrylate polymer) and CARBOPOL 971P® (cross-linked polyacrylate polymer). Most preferred is the use of Carbopol 971P® (cross-linked polyacrylate polymer). Among the copolymers of maleic anhydride and alkenyl derivative, are the copolymers EMA® (copolymers of maleic anhydride and ethylene; Monsanto). The dissolution of these polymers in water leads to an acid solution that will be neutralized, preferably to physiological pH, in order to give the adjuvant solution into which the immunogenic, immunological or vaccine composition itself will be incorporated.

Further suitable adjuvants include, but are not limited to, the RIBI® adjuvant system (preformed o/w emulsion containing monophosphoryl lipid A (MLA), trehalose dicorynomycolate (TDM), and cell wall skeleton from a tubercule *bacillus* (CWS); Ribi Inc.), Block co-polymer (CytRx, Atlanta Ga.), SAF-M® (threonyl N-acetyl-muramyl-L-alanyl-D-isoglutamine (MDP), squalane, L121® (block copolymer surfactant), and TWEEN 80® (polyoxyethylene (20) sorbitan monooleate); Chiron, Emeryville Calif.), monophosphoryl lipid A, AVRIDINE® (N,N-Dioctadecyl-N',N'-bis(2-hydroxyethyl)-1,3-diaminopropane, N,N-Dioctadeql-N',N'-bis(2-hydroxyethyl)propanediamine) lipid-amine adjuvant, heat-labile enterotoxin from *E. coli* (recombinant or otherwise), cholera toxin, IMS 1314® (liquid nanoparticle dispersion) or muramyl dipeptide, or naturally occurring or recombinant cytokines or analogs thereof or stimulants of endogenous cytokine release, among many others.

"Diluents" can include water, saline, dextrose, ethanol, glycerol, and the like. Isotonic agents can include sodium chloride, dextrose, mannitol, sorbitol, and lactose, among others. Stabilizers include albumin and alkali salts of ethylendiamintetracetic acid, among others.

"Vaccine matrix" or "formulation matrix" or "background matrix" all refer to the adjuvants, excipients, diluents, isotonic agents, stabilizers or other materials in a vaccine formulated for injection into an animal, other than the specific antigen. Those materials may contain elements that interfere with the detection and/or accurate quantitation of a second vaccine antigen in a combination vaccine using a conventional assay, e.g., by the presence of antibodies from serum used in the manufacture of the vaccine component, or other materials which compete with the second vaccine antigen for binding, to antibodies used in an ELISA immunoassay.

Methods for Identification and Synthesis of Signature Peptides

General methods for identification and synthesis of signature peptides are known in the art, e.g., as described by WO200600281, the disclosure of which is incorporated herein by reference.

The invention provides a method for quantitative measurement of peptides generated from intact proteins of vaccines in complex mixtures containing components which interfere with specific-binding partner elements such as antibody-based ELISA assays, wherein the peptides are generated by enzymatic or chemical cleavage, using mass-labeled signature peptides. The mass-labeled signature peptide contains an identical or almost identical amino-acid sequence to the analyte vaccine protein fragment generated by such cleavage. Cleavage of the analyte vaccine protein yields an analyzable peptide from the protein, wherein the only difference between analyzable peptide and the mass-labeled signature peptide from an analytical perspective is a mass-shift of typically 2-10 Dalton.

By using a mass-shifted signature peptide, advantages are achieved: i) the internal standard precursor may be designed to co-purify with the analyte protein or analyte peptide during any of various optional sample preparations steps performed prior to protein fragmentation; and ii) a single internal standard precursor may be designed to generate internal standard peptides for analysis of peptide fragments originating from several different analyte proteins or analyte peptides.

The mass-labeled signature peptide can be generated by peptide synthesis, during which one or more mass-labeled amino acids are incorporated. Preferably, the mass-label amino acids contain of one or more stable isotopes, including but not limited to $^{13}C$, $^{15}N$, $^{18}O$, $^{2}H$, and $^{34}S$.

Peptides may be synthesized by the Fmoc-polyamide mode of solid-phase peptide synthesis as disclosed by Lu et al., (1981) J. Org. Chem. 46, 3433 and references therein. Temporary N-amino group protection is afforded by the 9-fluorenylmethyloxycarbonyl (Fmoc) group. Repetitive cleavage of this highly base-labile protecting group is affected using 20% piperidine in N5N-dimethylformamide. Side-chain functionalities may be protected as their butyl ethers (in the case of serine threonine and tyrosine), butyl esters (in the case of glutamic acid and aspartic acid), butyloxycarbonyl derivative (in the case of lysine and histidine), trityl derivative (in the case of cysteine) and 4-methoxy-2,3,6-trimethylbenzenesulphonyl derivative (in the case of arginine). Where glutamine or asparagine are C-terminal residues, use is made of the 4,4'-diinethoxybenzhydryl group for protection of the side chain amido functionalities. The solid-phase support is based on a polydimethyl-acrylamide polymer constituted from the three monomers dimethylacrylamide (backbone-monomer), bisacryloylethyiene diamine (cross linlcer) and acryloylsarcosine methyl ester (functionalising agent). The peptide-to-resin cleavable linked agent used is the acid-labile 4-hydroxymethyl-phenoxyacetic acid derivative. All amino acid derivatives are added as their preformed symmetrical anhydride derivatives with the exception of asparagine and glutamine, which are added using a reversed N,N-dicyclohexyl-carbodiimide/1-hydroxybenzotriazole mediated coupling procedure. All coupling and deprotection reactions are monitored using ninhydrin, trinitrobenzene sulphonic acid or isotin test procedures. Upon completion of synthesis, peptides are cleaved from the resin support with concomitant removal of side-chain protecting groups by treatment with 95% trifluoroacetic acid containing a 50% scavenger mix. Scavengers commonly used are ethanedithiol, phenol, anisole and water, the exact choice depending on the constituent amino acids of the peptide being synthesized. Trifluoroacetic acid is removed by evaporation in vacuo, with subsequent trituration with diethyl ether affording the crude peptide. Any scavengers present are removed by a simple extraction procedure which on lyophilisation of the aqueous phase affords the crude peptide free of scavengers. Reagents for peptide synthesis are generally available from Calbiochem-Novabiochem (UK) Ltd, Nottingham NG7 2QJ, UK. Purification may be effected by any one, or a combination of, techniques such as size exclusion chromatography, ion-exchange chromatography and (principally) reverse-phase high performance liquid chromatography. Analysis of peptides may be carried out using thin layer chromatography, reverse-phase high performance liquid chromatography, amino acid analysis after acid hydrolysis and by fast atom bombardment (FAB) mass spectrometric analysis.

The mass label may also consist of other chemical modifications of the amino acids including, but not limited to, acetylation, methylation, deamidation and carboxymethylation. If the mass label modification is other than incorporation of stable isotopes, it is important to avoid modifications that may alter the internal standard peptides behavior during sample preparation, separation and ionization.

Furthermore, the mass-labeled signature peptide may be synthesized to have one or more replacement amino acid residues with reference to the analyte protein or peptide; for example, an alanine in replacement of a glycine. In such a circumstance, cleavage of the analyte protein or peptide and the mass-labeled peptide internal standard precursor will yield an analyzable peptide from the protein and an internal standard peptide from the internal standard precursor, the only difference between them from an analytical perspective being a mass-shift due to the presence of alanine in the peptide internal standard relative to the presence of glycine in the analyte protein or peptide. An advantage of such an embodiment of the invention is that it may be easier to replace an alanine with a glycine rather than with an isotopic-labeled alanine during synthesis of the mass-labeled peptide internal standard precursor. Further suitable amino acid replacements can be readily appreciated by a person of skill in the art, for example valine and isoleucine may be interchanged.

The mass-labeled peptide internal standard precursor may have no, one, two, three, four or five replacement amino acid residues with reference to the analyte protein or peptide, or may differ in up to five, ten, fifteen, twenty or twenty-five percent of the total number of amino acid residues with reference to the analyte protein or peptide. Preferably the mass-labeled signature peptide has no or one replacement amino acid residue with reference to the analyte protein or peptide.

If the analyte protein fragment contains any posttranslational modifications such as phosphorylation, the mass-labeled signature peptide may be synthesized to be identically modified.

The mass-labeled peptide internal standard precursors may also be generated by recombinant protein expression in the presence of mass-labeled amino acids as a part of a hybrid protein, in which case the hybrid protein as such can constitute the internal standard precursor or the hybrid protein may be processed to yield one or more peptide internal standard precursors.

In preparing a mass-labeled signature peptide using recombinant protein expression, a DNA molecule is prepared that encodes the desired peptide using methods well known to those skilled in the art and exemplified by Sambrook et al. (2001) "Molecular Cloning, a Laboratory Manual", 3rd edition, Sambrook et. al. (eds), Cold Spring Harbor Laboratory Press, Cold Spring Harbor, N.Y., USA.

The DNA is then expressed in a suitable host to produce a mass-labeled peptide internal standard precursor. Thus, the DNA encoding the said peptide may be used in accordance with known techniques, appropriately modified in view of the teachings contained herein, to construct an expression vector, which is then used to transform an appropriate host cell for the expression and production of the said peptide. Such techniques include those disclosed in U.S. Pat. No. 4,440,859 issued 3 Apr. 1984 to Rutter et al., U.S. Pat. No. 4,530,901 issued 23 Jul. 1985 to Weissman, U.S. Pat. No. 4,582,800 issued 15 Apr. 1986 to Crowl, U.S. Pat. No. 4,677,063 issued 30 Jun. 1987 to Mark et al., U.S. Pat. No. 4,678,751 issued 7 Jul. 1987 to Goeddel, U.S. Pat. No. 4,704,362 issued 3 Nov. 1987 to Itakura et al., U.S. Pat. No. 4,710,463 issued 1 Dec. 1987 to Murray, U.S. Pat. No. 4,757,006 issued 12 Jul. 1988 to Toole, Jr. et al., U.S. Pat. No. 4,766,075 issued 23 Aug. 1988 to Goeddel et al. and 4,810,648 issued 7 Mar. 1989 to Stalker, all of which are incorporated herein by reference.

The DNA encoding a mass-labeled signature peptide may be joined to a wide variety of other DNA sequences for introduction into an appropriate host. The companion DNA will depend upon the nature of the host, the manner of the introduction of the DNA into the host, and whether episomal maintenance or integration is desired.

Generally, the DNA is inserted into an expression vector, such as a plasmid, in proper orientation and correct reading frame for expression. A preferred expression vector is a baculovirus, most preferably from a commercially available system. If necessary, the DNA may be linked to the appropriate transcriptional and translational regulatory control nucleotide sequences recognized by the desired host, although such controls are generally available in the expression vector. Thus, the DNA insert may be operatively linked to an appropriate promoter. Bacterial promoters include the *E. coli* lad and lacZ promoters, the T3 and T7 promoters, the gpt promoter, the phage λ PR and PL promoters, the phoA promoter and the trp promoter. Eukaryotic promoters include the CMV immediate early promoter, the HSV thymidine kinase promoter, the early and late SV40 promoters and the promoters of retroviral LTRs. Other suitable promoters will be known to the skilled artisan. The expression constructs will desirably also contain sites for transcription initiation and termination, and in the transcribed region, a ribosome binding site for translation. (Hastings et al., International Patent No. WO 98/16643, published 23 Apr. 1998)

The vector is then introduced into the host through standard techniques. Generally, not all of the hosts will be transformed by the vector and it will therefore be necessary to select for transformed host cells. One selection technique involves incorporating into the expression vector a DNA sequence marker, with any necessary control elements, that codes for a selectable trait in the transformed cell. These markers include dihydrofolate reductase, G418 or neomycin resistance for eukaryotic cell culture, and tetracyclin, kanamycin or ampicillin resistance genes for culturing in *E. coli* and other bacteria. Alternatively, the gene for such selectable trait can be on another vector, which is used to co-transform the desired host cell.

Host cells that have been transformed by the recombinant DNA encoding a mass-labeled signature peptide are then cultured for a sufficient time and under appropriate conditions known to those skilled in the art permit the expression of the polypeptide, which can then be recovered.

The a mass-labeled signature peptide can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification.

Many expression systems are known, including systems employing: bacteria (e.g., *E. coli* and *Bacillus subtilis*) transformed with, for example, recombinant bacteriophage, plasmid or cosmid DNA expression vectors; yeasts (e.g., *Saccaromyces cerevisiae*) transformed with, for example, yeast expression vectors; insect cell systems transformed with, for example, viral expression vectors (e.g., baculovirus); plant cell systems transfected with, for example viral or bacterial expression vectors; animal cell systems transfected with, for example, adenovirus expression vectors.

Suitable amino acid sequences for use as a mass-labeled peptide internal standard may be determined by predicting fragmentation products of a protein based on the specificity of the protein and the analyte protein's amino acid sequence using in silico methods well known to those skilled in the art. The amino acid sequence or sequences suitable for use as peptide internal standard precursors may also be determined by fragmentation and mass spectrometric analysis of the analyte protein and the actual primary structure of the generated peptide fragments are determined.

The analyte protein can be any known protein or a hypothetical protein predicted by analysis of nucleic acid sequences of a vaccine.

The mass-labeled signature peptide may be designed to detect and measure modified proteins and the peptides, where the modifications include but are not limited to phosphorylation, glycosylation, oxidation, farnesylation, acetylation, ubiquination, lipidation, prenylation and sulfonation. They may also be designed to detect and measure known or predicted protein and peptide species generated by alternative splicing of mRNA, by specific or unspecific degradation of the protein in vivo or by variation due to single nucleotide polymorphisms.

A single signature peptide may be designed and synthesized to generate one, two or more signature peptides upon cleavage. Hence a further embodiment of this aspect of the invention is wherein a mass-labeled signature peptide comprises more than one mass-labeled signature peptide. A further embodiment of this aspect of the invention is wherein a mass-labeled signature peptide comprises mass-labeled peptide internal standards for analysis of peptide fragments originating from multiple analyte proteins.

A heterogeneous sample of peptides or proteins may be extracted from a vaccine sample, or derived from fragmentation of a heterogeneous sample of peptides and proteins extracted form a vaccine sample. Methods of extracting proteins from such vaccine samples are well known to those skilled in the art.

The mass-labeled signature peptide useful in this aspect of the invention can be any length that is suitable for the method of the invention and are typically of a length of between 4 and 50 amino acids, preferably a length of between 10 and 40 amino acids. The size of the mass-labeled signature peptide is dictated by the requirement for the signature peptide to have a minimum size such that it can be related to the analyte protein or peptide and a maximum size such that the standard peptide can be resolved using existing methods of mass spectrometry.

A further embodiment of this aspect of the invention is wherein the mass-labeled peptide internal standard precursor has a length of between 6 and 200 amino acids. As mentioned above the signature peptide precursor may contain one or several amino acid sequences which corresponds to sequences in one or several known or predicted proteins.

A further embodiment of this aspect of the invention is wherein the mass-labeled signature peptide co-purifies with the analyte protein or analyte proteins to be measured during sample preparation steps performed prior to exposure to enzymatic or chemical cleavage.

The mass-shifted signature peptide is added to the sample to be analyzed, optionally prior to any sample preparation or fractionation steps. Several different signature peptides may be added to allow quantification of multiple different protein and peptides simultaneously, and several internal standard precursors can be added for different fragments from the same protein to obtain redundant information. Alternatively, a single internal standard precursor generating more than one internal standard may be used.

The sample can be, if required, prepared for analysis by removing substances that may interfere with the analysis and to enrich the analyte(s). Methods that may be used include solid phase extraction, liquid chromatography, precipitation, ultra filtration and purification using affinity-based techniques, as would be appreciated to those skilled in the art.

The proteins in the sample may also be chemically modified, for example by reduction and carboxymethylation of cysteines to break disulfide bridges and avoid formation of peptide dimers.

The method of the invention comprises the step of fragmenting the heterogeneous sample of proteins or peptides to produce a heterogeneous sample of peptide fragments. These fragments then may be identified and analyzed using methods and processes associated with multiple reaction monitoring mass spectrometry, disclosed in greater detail below.

The step of fragmenting of the heterogeneous sample of proteins, polypeptides or peptides may be achieved by any method known in the art. For example, chemical or enzymatic cleavage may be used. Numerous methods of chemical or enzymatic (i.e., protease directed) cleavage are known in the art. For example, proteases include trypsin, clrymotrypsin, pepsin, thrombin, papain, bromelain, thermolysin, subtilisin, Factor Xa, *Staphylococcus aureus* protease and carboxypeptidase A. In a preferred embodiment, the fragmentation method will cleave proteins, polypeptides or peptides at defined locations. Enzymatic cleavage is typically sequence-directed, as shown below. Hence a further embodiment of this aspect of the invention is wherein the enzymatic or chemical cleavage is sequence-directed.

| Enzyme: | Preferred Cleavage Site |
|---|---|
| trypsin: | R1 = Lys, Arg |
| chymotrypsin: | R1 = Tyr, Phe, Leu, Ile, Val, Trp and His at high pH |
| pepsin: | R1 = Phe, Leu, many others |
| thrombin: | R1 = Arg |
| papain: | R1 = Arg, Lys, Phe-X (CO side of residue next to Phe) |
| bromelain: | R1 = Lys, Ala, Tyr, Gly |
| *Staphylococcus aureus* protease: | R1 = Glu, Asp |
| Factor Xa: | R1 = Ile-Glu-Gly-Arg |
| Thermolysin: | R2 = Tyr, Phe, Leu, Ile, Val, Trp and His | wherein R1 and R2 are defined according to the following formula:

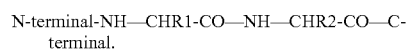

N-terminal-NH—CHR1-CO—NH—CHR2-CO—C-terminal.

Chemical cleavage methods may also be sequence-directed e.g., cyanogen bromide fragmentation, which will cleave a protein or peptide on the C-terminal side of methionine.

Thus, for example, trypsin cleavage is a sequence-directed means of fragmentation, since cleavage is directed by the presence of arginine or lysine residues in a protein, polypeptide or peptide, and accordingly produces cleavage fragments that have, as their C-terminal residue, either an arginine or lysine.

A further embodiment of this aspect of this invention is wherein the mass-labeled peptide internal standard precursor and sample comprising one or multiple analyte proteins are separated after enzymatic or chemical cleavage.

Fragmentation of a heterogeneous protein population into peptides will usually yield a highly complex mixture of peptides that requires separation to prior mass spectrometric analysis to reduce the complexity. Methods that may be used for peptide separation include liquid chromatography (in one or more separation dimensions), solid phase extraction and affinity capture, as would be appreciated by a person skilled in the art.

The separation can be coupled to mass spectrometric analysis either on-line (liquid chromatography coupled to electrospray mass spectrometry) or by fractionation followed by analysis of the individual fraction by e.g., matrix assisted laser desorption/ionization mass spectrometry (MALDI). The difference in abundance between the analyte peptide and the mass-labeled internal standard peptide can be measured either by single-stage mass spectrometry (MS) or multi-stage MS (MS/MS or MS"). In a two-stage mass spectrometric analysis, the first mass separation is used to select the peptides to be analyzed, the selected peptides are then fragmented and the fragments analyzed in the second-stage mass separation.

MS/MS is a very powerful approach for analyzing complex peptide mixtures as it has the potential of resolving peptides with identical molecular mass but with different amino acid composition.

The intensity of the signal obtained from a specific peptide by mass spectrometry is dependent on the concentration, molecular weight and ionization characteristics of the peptide as well as quenching effects of other components in the sample. For two peptides that are identical apart from e.g., isotopic composition, the relative signal intensity should ideally depend only on the concentrations, as all other factors should affect them equally.

Another method for separating peptides is 'Signature Peptide Capture' (SPC) as set out in PCT/EP2004/002566 and herein incorporated by reference.

A further aspect of the invention provides a kit of parts comprising a mass-labeled signature peptide as defined in above or in relation to the first aspect of the invention and an agent for fragmenting peptides.

A further aspect of the invention provides a kit of parts comprising a mass-labeled signature peptide as defined in above or in relation to the first aspect of the invention and a test sample containing or to be tested for (for example thought to contain) the analyte protein or peptide. The kit may further comprise an agent for fragmenting peptides.

Mass Spectrometry

Mass spectrometry may be used to display the spectra of the masses of the molecules comprising the sample, including mass of targeted signature peptides. Mass spectrometry also may be referred to as mass spectroscopy. Mass spectrometry includes the following steps:
 a. ionizing the sample including the signature peptides added to the viral protein;
 b. separating the ions generated according to their mass-to-charge ration;
 c. dynamically detecting the ions by detecting the energy of the charged particles; and
 d. processing the resultant signal or plurality of signals into the spectra of the masses of the particles of the sample.

Systems and devices capable of performing mass spectrum analysis may be shown in *An Introduction to Mass Spectrometry* (1997), Van Bramer, Widener University, Department of Chemistry, herein incorporated by reference. Multiple reaction monitoring (MRM) mass spectrometry is employed by the disclosed embodiments to enhance the detection process. Unlike traditional mass spectrometry, MRM is highly selective and targeted. This feature allows an instrument to be fine-tuned to specifically look for protein fragments of interest. Thus, the disclosed embodiments provide targeted analysis of proteins of interest as opposed to large amounts of data generated from the usual mass spectral analysis.

The quantification of the presence of one or more viral proteins in the sample may be detected differentially by the disclosed embodiments using multiple reaction monitoring. Fragments of the proteins may be identified, and then a "filtering" process performed to quantify those proteins of interest. According to these embodiments, a triple quadrupole mass spectrometer maybe used for quantitative measurement of targeted proteins. For example, the MRM process may use at least two stages of mass filtering to examine selectively the fragmentation of particular ions related to the viral proteins. In one stage, an ion of interest (the precursor) is preselected, and induced to fragment in a collision cell. In a second stage, a small number of sequence-specific fragment ions, or transition ions, are mass analyzed. Thus, the disclosed embodiments may use MRM to determine the amount of the viral protein in the vaccine preparation sample by comparing the results of the MRM analyses with standards.

The system and process used by MRM mass spectrometry may be disclosed by "Quantitative, Multiplexed Assays for Low Abundance Proteins in Plasma by Targeted Mass Spectrometry and Stable Isotope Dilution," Keshishian et al., Mol Cell Proteomics 6:2212-29 (2007), herein incorporated by reference. Other embodiments may be used with the function of filtering the ions generated by the MRM process according to their mass, and providing a spectral analysis of these ions.

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

The contents of all patents, patent application and publications which are recited above and below are hereby incorporated by reference herein, in their entirety.

EXAMPLES

Example 1: Development of Assay to Quantitatively Determine Concentration of PCV OR2 in a Vaccine Composition We have successfully developed an assay to quantitatively measure ORF2 protein in a complex matrix. By monitoring multiple reaction monitoring (MRM) transitions of two signature tryptic peptides of this ORF2 protein: NVD-HVGLGTAFENSK (SEQ ID NO:4) and VEFWPC-SPITQGDR (SEQ ID NO:24), we were able to build linear standard curves in the range of 3.125 µg/mL to 200 µg/mL, with coefficient of variance (CV) less than 10% for all but one point in the standard curve, including both all sample processing and analytical equipment performance. This concentration range was set prior to conducting the measurements in anticipation of the needed dynamic range; the signal-to-noise however is sufficient to extend the Lower Limit of Quantification (LLOQ) to lower concentrations in future work if needed. The concentration determined for vaccine sample 230-61A (the lot number of the testing sample described below) is approximately 4 µg/mL.

Serial dilution curves were generated for 2 sets of vaccine (set 1: samples 261-007B-1, 261-007C-1, 261-007D-1 and 261-007F-1; set 2: 261-007B, 261-007C, 261-007D, and 261-007F). The MRM measurement was able to distinguish the slight concentration variation within each set of vaccine.

Materials The following samples were supplied by Boehringer Ingelheim Vetmedica.

They were aliquotted (50 µL/vial) and then maintained in a −80° C. freezer before processing.

Sample 1: 230-61A (The target sample comprises MYCOFLEX® (inactivated *Mycoplasma hyopneumoniae* bacterin vaccine) and MYCOFLEX® (inactivated *Mycoplasma hyopneumoniae* bacterin vaccine). The medium includes 10% porcine serum.)

Sample 2: 230-61B (A positive control. It also contains the ORF2 protein.)

Sample 3: 230-61C (A background matrix of 230-61B. It does not contain ORF2.)

Sample 4: 230-61D (Purified ORF2 in PBS buffer)

Sample 5: 230-64E (A background matrix of 230-61A.)

Sample 6: 230-64F (*Mycoplasma hyopneumoniae*. The medium includes: 10% porcine serum.)

In addition, a purified ORF2 sample at 1 mg/mL was provided to generate a standard curve.

Three stable-isotope-labeled synthetic peptides (denoted as "AQUA" peptides) representing the three tryptic sequences of the ORF2 were purchased from AnaSpec (Fremont, Calif.) at 5×1 nmol quantity. The three peptides are:

a. NVDHVGLGTAFENS[KC$^{13}$N$^{15}$], (SEQ ID NO: 4)

b. ISIPFEYYM[RC$^{13}$N$^{15}$], (SEQ ID NO: 26)
and c. VEFWPCSPITQGD[RC$^{13}$N$^{15}$]. (SEQ ID NO: 24)

The isotope label was at the C-terminal amino acid. The label on lysine results in a mass shift of 8 Da and the label on arginine results in a mass shift of 10 Da. In addition to the three AQUA peptides, a longer peptide containing the sequence of ISIPFEYYR (SEQ ID NO:26) was synthesized for determining the tryptic digest efficiency. This peptide is GGGTNK[IC$^{13}$N$^{13}$]S[IC$^{13}$N$^{15}$]PFEYYRIRKVKVEF (SEQ ID NO:28). Labels on two isoleucines result in a mass shift of 14 Da RAPIGEST® detergent (sodium 3-[(2-methyl-2-undecyl-1,3-dioxolan-4-yl)methoxy]-1-propanesulfonate) was purchased from Waters (Milford, Mass.).

Methods

Sample Preparation for Standard Curve.

ORF2 (1 mg/mL) was spiked into the background matrix of the vaccine "sample 5, 230-64E" to a final concentration of 200 µg/mL. Using this stock solution, a serial dilution was made by adding "sample 5, 230-64E" to generate the following pre-determined ORF2 concentrations: 100, 50, 25, 12.5, 6.25, and 3.125 µg/mL. In addition, three other concentrations, 64, 32 and 16 µg/mL, were made for the purpose of validation.

Tryptic Digestion of standard curve samples and Vaccine

Typically, 20 µL of sample was diluted with 80 µL MASTERMIX® solution containing 50 mM NH$_4$HCO$_3$, 0.1% RAPIGEST® (sodium 3-[(2-methyl-2-undecyl-1,3-dioxolan-4-yl)methoxy]-1-propanesulfonate), 250 fmol/µL of AQUA peptides with stable-isotope-labeled amino acid. The four AQUA peptides are NVDHVGLGTAFENS[KC$^{13}$N$^{15}$] (SEQ ID NO:4), ISIPFEYY[RC$^{13}$N$^{15}$] (SEQ ID NO:4), VEFWPCSPITQGD[RC$^{13}$N$^{15}$] (SEQ ID NO:24), and GGGTNK[IC$^{13}$N$^{15}$]S[IC$^{13}$N$^{15}$]PFEYYRIRKVKVEF (SEQ ID NO:28). In the case of a double blank sample, AQUA peptides were not included in the MASTERMIX® solution.

Subsequently, the proteins were denatured, reduced, and alkylated before being digested by 8 µg trypsin at 37° C. for 16 hours. Finally, this solution containing the tryptic peptides of ORF2 and AQUA peptides were acidified to break down the RAPIGEST® detergent (sodium 3-[(2-methyl-2-undecyl-1,3-dioxol an-4-yl)methoxy]-1-propanesulfonate) and analyzed by LC-MRM on a 4000 Qtrap triple quadrupole instrument (ABI/Sciex).

Liquid-Chromatograph-MRM (LC-MRM)

A binary Agilent capillary-1100 series HPLC system was directly coupled to a ABI 4000 Qtrap mass spectrometer. A capillary reverse-phase chromatography column (5-µm C18 silica particles, column dimension 320 µm×15 cm, Micro-Tech Scientific, Vista, Calif.) was used at a flow rate of 8 µL/min. Injection volume was 10 µL for all runs using a Leap Technologies (Carrboro, N.C.) model HTC PAL autosampler. Gradient elution of the tryptic peptides was achieved using a gradient of 0% to 45% solvent B over 52 min (solvent A is 0.1% formic acid in H2O and solvent B is 0.1% formic acid in acetonitrile). The MRM conditions were determined by infusing the AQUA peptides and ramping up the declustering potential (DP) and collision energy (CE) to maximize fragment ion intensities. Final conditions are listed in Table 1. The dwell time for each transition was set at 50 ms and the total Qtrap cycle time was 0.77 sec.

TABLE 1

MRM conditions for the three ORF2 tryptic peptides and their corresponding AQUA peptides.

| Q1 | Q3 | Dwell Time (msec) | Peptide | DP | CE |
|---|---|---|---|---|---|
| 794.4 | 1023.5 | 50 | NVDHVGLGTAFENSK | 100 | 42 |
| 794.4 | 853.4 | 50 | NVDHVGLGTAFENSK | 100 | 40 |

TABLE 1-continued

MRM conditions for the three ORF2 tryptic peptides and their corresponding AQUA peptides.

| Q1 | Q3 | Dwell Time (msec) | Peptide | DP | CE |
|---|---|---|---|---|---|
| 798.4 | 1031.5 | 50 | NVDHVGLGTAFENSK* | 100 | 42 |
| 798.4 | 861.4 | 50 | NVDHVGLGTAFENSK* | 100 | 40 |
| 594.3 | 874.4 | 50 | ISIPFEYYR | 70 | 25 |
| 594.3 | 987.5 | 50 | ISIPFEYYR | 70 | 24 |
| 599.3 | 884.4 | 50 | ISIPFEYYR* | 70 | 25 |
| 599.3 | 997.5 | 50 | ISIPFEYYR* | 70 | 24 |
| 601.3 | 874.4 | 50 | I*SI*PFEYYR | 70 | 25 |
| 601.3 | 994.5 | 50 | I*SI*PFEYYR | 70 | 24 |
| 846.9 | 1131.5 | 50 | VEFWPC(carboxymethyl)SPITQGDR | 80 | 37 |
| 846.9 | 786.4 | 50 | VEFWPC(carboxymethyl)SPITQGDR | 80 | 40 |
| 851.9 | 1141.5 | 50 | VEFWPC(carboxymethyl)SPITQGDR* | 80 | 37 |
| 851.9 | 796.5 | 50 | VEFWPC(carboxymethyl)SPITQGDR* | 80 | 40 |

K* is $C^{13}N^{15}$ labeled lysine, R* $C^{13}N^{15}$ labeled arginine, and I* is $C^{13}N^{15}$ labeled isoleucine. The mass increase for the labeled amino acid is 8 Da, 10 Da, and 7 Da respectively.

Calibration Standard Curves, Validation, and Determination of ORF2 Concentrations in Vaccine Calibration standard curves were generated with the ORF2 spiked into "sample 5, 230-64E" to the predetermined final concentrations of 3.125, 6.25, 12.5, 25, 50, 100, and 200 µg/mL. The AQUA peptides (200 fmol/µL) were added to the elution solution for each concentration point to serve as internal standards. The peak area responses recorded for transition were integrated using the ABI MultiQuant Software (version 1.0, AB SCIEX, 500 Old Connecticut Path, Framingham, Mass. 01701, USA). The integration parameters for all peptides were set at the followings: total smoothing width, 3 points; RT window, 120 sec; min. peak width, 3 pints; min. peak height, 0 cps; noise percentage, 40%; baseline sub. window, 2 min; peak splitting factor, 2 points. The integrated peak area ratios Cv axis) of the ORF2 peptide to AQUA peptide were plotted against the concentration of the ORF2 (x axis) and linearly fit standard curves were derived (y=mx+b). ORF2 vaccine concentrations and the validation samples at 64, 32 and 16 µg/mL were calculated using the standard curve.

Vaccine Serial Dilution Curves

Vaccines 261-007B-1, 261-007C-1, 261-007D-1, 261-007F-1 was diluted 2, 4, 8, 16, and 32 fold using sample 230-64E. Vaccines 261-007B, 261-007C, 261-007D, 261-007F were diluted 2, 4, 8, 16, and 32 fold using sample 230-61C. The diluted and the undiluted samples were processed and analyzed using the same protocol as described above.

Results

Selection of Tryptic Peptides for MRM Monitoring

The tryptic digest of the purified ORF2 protein was analyzed on an Orbitrap mass spectrometer for peptide identification. Three tryptic sequences were selected for AQUA peptide synthesis as well as MRM monitoring because of their strong and relatively clean signal characteristics. Each peptide was monitored at two y-ion transitions (see Table 1). In addition, an extended version (GGGTNK[IC$^{13}$N$^{15}$]s[IC$^{13}$N$^{15}$]PFEYYRIRKVKVEF) (SEQ ID NO:28) of peptide ISIPFEYYR (SEQ ID NO:26) was synthesized. This peptide contained two tryptic cleavage sites. The signal ratio of stable-isotope-labeled peptide [IC$^{13}$N$^{15}$]S[IC$^{13}$N$^{15}$]PFEYYR (SEQ ID NO:4) to peptide ISIPFEYY[RC$^{13}$N$^{15}$] (SEQ ID NO:4) was calculated to estimate the digestion efficiency. In the result section, we will only discuss data related to peptides NVDHVGLGTAFENSK (SEQ ID NO:4) and VEFWPCSPITQGDR (SEQ ID NO:24). Peptide ISIPFEYYR (SEQ ID NO:26) is discussed in the DISCUSSION section.

Standard Curves

Figure 2:
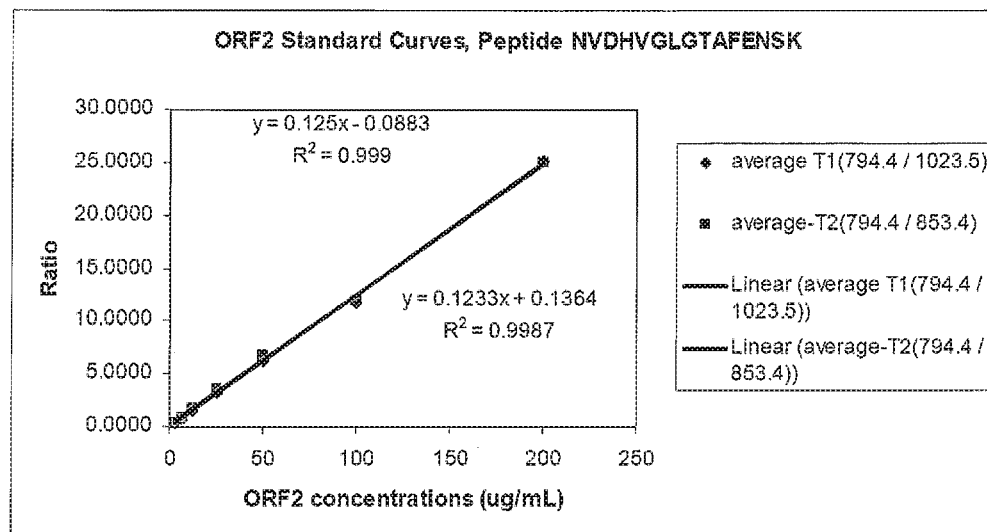
FIG. 2: Standard curves for ORF2. Spiked in ORF2 concentrations were plotted on x-axis. The peak area ratios of the ORF2 peptide to AQUA peptide were plotted on the y-axis. (a) standard curves for peptide NVDHVGLGTAFENSK (SEQ ID NO:4), including both transition 1 (T1) and transition 2 (T2); (b) standard curve for peptide VEFWPCSPITQGDR (SEQ ID NO:24), including both transition 1 (T1) and transition 2 (T2).
Figure 2:
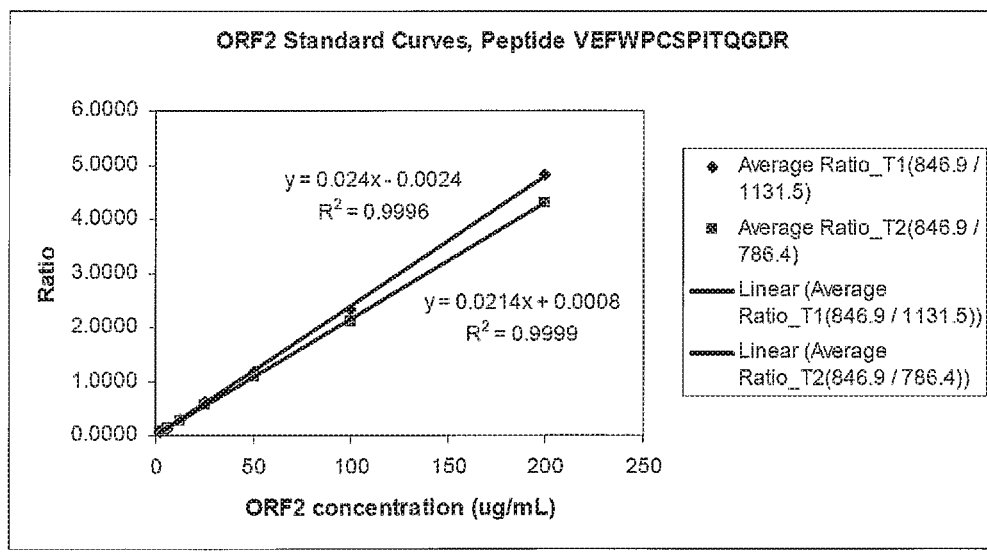

Four standard curves were generated for transitions 794.4/1023.5, 794.4/853.4, 846.9/1131.5 and 846.9/786.4 for peptides NVDHVGLGTAFENSK (SEQ ID NO:4) and VEFWPCSPITQGDR (SEQ ID NO:24), respectively. No data points were weighted. A simple linear fit was applied to all data points. The R-square for each curve was above 0.99. The coefficients of variance (CVs) for the three repeat samples (including all processing steps) range from 1% to 12%, with most data under 10%. FIG. 1 shows the integration for transition at 794.4/1023.5 and 794.4/853.4 from one set of data points. See FIG. 2 for the standard curves, Table 2 for the average ratios and calculated CVs, and Table 3 for calculated percentage of errors.

TABLE 2

Average ratios to the spiked AQUA peptide intensity and CVs for the standard curves.
(a) data for peptide NVDHVGLGTAEENSK (SEQ ID NO: 4);
(b) data for peptide VEFWPCSPITQGDR (SEQ ID NO: 24).

(a)

| Concentration (ug/mL) | average T1 (794.4/1023.5) | standard deviation-T1 | Coefficient of Variance-T1 (%) | average-T2 (794.4/853.4) | standard deviation-T2 | Coefficient of Variance-T2 (%) |
|---|---|---|---|---|---|---|
| 3.125 | 0.36 | 0.02 | 6 | 0.38 | 0.05 | 12 |
| 6.25 | 0.72 | 0.03 | 5 | 0.78 | 0.04 | 5 |
| 12.5 | 1.54 | 0.11 | 7 | 1.71 | 0.06 | 4 |
| 25 | 3.21 | 0.03 | 1 | 3.52 | 0.26 | 7 |
| 50 | 6.19 | 0.30 | 5 | 6.66 | 0.21 | 3 |
| 100 | 11.79 | 0.75 | 6 | 11.88 | 0.43 | 4 |
| 200 | 25.18 | 1.86 | 7 | 24.97 | 2.18 | 9 |

(b)

| Concentration (ug/mL) | Average Ratio_T1 (846.9/1131.5) | standard deviation-T1 | Coefficient of Variance-T1 (%) | Average Ratio_T2 (846.9/786.4) | standard deviation-T2 | Coefficient of Variance-T2 (%) |
|---|---|---|---|---|---|---|
| 3.125 | 0.07 | 0.00 | 5 | 0.06 | 0.00 | 6 |
| 6.25 | 0.15 | 0.01 | 5 | 0.13 | 0.01 | 4 |
| 12.5 | 0.30 | 0.01 | 3 | 0.26 | 0.00 | 1 |
| 25 | 0.64 | 0.01 | 1 | 0.56 | 0.02 | 4 |
| 50 | 1.19 | 0.01 | 1 | 1.08 | 0.03 | 3 |
| 100 | 2.33 | 0.05 | 2 | 2.11 | 0.06 | 3 |
| 200 | 4.82 | 0.11 | 2 | 4.30 | 0.11 | 3 |

Using the derived standard curves, the percentage of error was calculated for each concentration point (Table 3). Except for the lowest concentration of peptide NVDHVGLGTAFENSK (SEQ ID NO:4), the absolute values of the percentage of error range from 1% to 22%, with most data under 15%.

TABLE 3

Percentage of error for each concentration point used in the standard curve.
(a) data for peptide NVDHVGLGTAFENSK (SEQ ID NO: 4);
(b) data for peptide VEFWPCSPITQGDR (SEQ ID NO: 24).

| Concentration (mg/mL) | % of Error-T1_set 1 | % of Error-T2_set 1 | % of Error-T1_set 2 | % of Error-T2_set 2 | % of Error-T1_set 3 | % of Error-T2_set 3 |
|---|---|---|---|---|---|---|
| (a) | | | | | | |
| 3.125 | 20 | −24 | 12 | −49 | 9 | −39 |
| 6.25 | 8 | −13 | 2 | −22 | 0 | −13 |
| 12.5 | 8 | 6 | 9 | −1 | −4 | 0 |
| 25 | 6 | 17 | 5 | 0 | 4 | 13 |
| 50 | −5 | 9 | 4 | 7 | 3 | 2 |
| 100 | −8 | −3 | −9 | −9 | 2 | −2 |
| 200 | 7 | −2 | 3 | 11 | −7 | −7 |
| (b) | | | | | | |
| 3.125 | 0 | −2 | −8 | −13 | −6 | −9 |
| 6.25 | 5 | 2 | −5 | 2 | −2 | −5 |
| 12.5 | 5 | −1 | 1 | −1 | 0 | −3 |
| 25 | 8 | 8 | 5 | 0 | 7 | 6 |
| 50 | −1 | −1 | −1 | 0 | 0 | 4 |
| 100 | −2 | −2 | −5 | −4 | −1 | 1 |
| 200 | 2 | 0 | 2 | 3 | −2 | −2 |

Validation of the Standard Curves

Three QC solutions with ORF2 concentrations at 16 µg/mL, 32 µg/mL and 64 µg/mL were used to validate the curve. Each concentration point was processed and analyzed independently three times. The CVs for data were less than 8%. The absolute values of the percentage of error range from 1% to 12%, with most data under 10% (Table 4).

TABLE 4

Percentage of error for validation QC samples.
(a) data derived from peptide NVDHVGLGTAFENSK (SEQ ID NO: 4) standard curves.
(b) data derived from peptide VEFWPCSPITQGDR (SEQ ID NO: 24) standard curves.

(a)

| Sample Name | Ratio_T1 (794.4/ 1023.5) | Ratio_T2 (794.4/ 853.4) | Sample Calculated Conc_T1 (ug/mL) | Sample Calculated Conc_T2 (ug/mL) | average_T1 (ug/mL) | average_T2 (ug/mL) | stdev_T1 | stdev_T2 | CV-T1 | CV-T2 | % Error_T1 | % Error_T2 |
|---|---|---|---|---|---|---|---|---|---|---|---|---|
| I1_64 | 8.07 | 8.16 | 65.24 | 65.08 | 64.23 | 67.42 | 2.50 | 2.06 | 4 | 3 | 2 | 2 |
| I2_64 | 7.59 | 8.55 | 61.39 | 68.20 | | | | | | | — | 7 |
| I3_64 | 8.17 | 8.64 | 66.07 | 68.97 | | | | | | | 3 | 8 |
| J1_32 | 4.26 | 4.12 | 34.76 | 32.31 | 33.43 | 29.87 | 2.40 | 2.19 | 7 | 7 | 9 | 1 |
| J2_32 | 4.27 | 3.60 | 34.86 | 28.09 | | | | | | | 9 | −12 |
| J3_32 | 3.74 | 3.74 | 30.66 | 29.19 | | | | | | | — | −9 |
| K1_16 | 1.93 | 2.13 | 16.14 | 16.20 | 16.51 | 15.53 | 0.50 | 0.61 | 3 | 4 | 0 | 0 |
| K2_16 | 1.95 | 2.03 | 16.32 | 15.38 | | | | | | | 0 | −1 |
| K3_16 | 2.05 | 1.99 | 17.08 | 15.00 | | | | | | | 2 | −2 |

(b)

| Sample Name | Ratio_T1 (846.9/ 1131.5) | Ratio_T2 (846.9/ 786.4) | Sample Calculated Conc_T1 (ug/mL) | Sample Calculated Conc_T2 (ug/mL) | average_T1 (ug/mL) | average_T2 (ug/mL) | stdev_T1 | stdev_T2 | CV-T1 | CV-T2 | % Error_T1 | % Error_T2 |
|---|---|---|---|---|---|---|---|---|---|---|---|---|
| I1_64 | 1.53 | 1.35 | 63.66 | 63.06 | 64.86 | 63.84 | 1.05 | 0.84 | 2 | 1 | — | −1 |
| I2_64 | 1.57 | 1.36 | 65.35 | 63.74 | | | | | | | 2 | 0 |
| I3_64 | 1.57 | 1.39 | 65.57 | 64.72 | | | | | | | 2 | 1 |
| J1_32 | 0.81 | 0.73 | 34.02 | 33.94 | 31.97 | 31.59 | 1.90 | 2.49 | 6 | 8 | 6 | 6 |
| J2_32 | 0.76 | 0.68 | 31.65 | 31.85 | | | | | | | — | 0 |
| J3_32 | 0.72 | 0.62 | 30.25 | 28.99 | | | | | | | — | −9 |
| K1_16 | 0.39 | 0.35 | 16.50 | 16.30 | 16.54 | 16.45 | 0.63 | 0.78 | 4 | 5 | 1 | 0 |
| K2_16 | 0.38 | 0.34 | 15.93 | 15.76 | | | | | | | 0 | 0 |
| K3_16 | 0.41 | 0.37 | 17.18 | 17.29 | | | | | | | 2 | 2 |

ORF2 Concentration in Vaccine 230-61A

Vaccine 230-61A sample was processed and analyzed independently three times. The ORF2 concentration was determined using the standard curves derived from the peptides NVDHVGLGTAFENSK (SEQ ID NO:4) and VEFWPCSPITQGDR (SEQ ID NO:24). The absolute values and the CV are displayed in Table 5.

TABLE 5

Concentration of ORF2 protein in vaccine 230-61A.
(a) data derived from peptide NVDHVGLGTAFENSK (SEQ ID NO: 4) standard curves.
(b) data derived from peptide VEFWPCSPITQGDR (SEQ ID NO: 24) standard curves.

(a)

| Sample | Ratio_T1 (794.4/1023.5) | Ratio_T2 (794.4/853.4) | Sample Conc_T1 (ug/mL) | Sample Conc_T2 (ug/mL) | average_T1 (ug/mL) | average_T2 (ug/mL) | stdev_T1 | stdev_T2 | CV-T1 | CV-T2 |
|---|---|---|---|---|---|---|---|---|---|---|
| L1 | 0.9502 | 0.9502 | 8.31 | 6.60 | 8.45 | 6.49 | 0.36 | 0.21 | 4 | 3 |
| L2 | 1.0188 | 0.9068 | 8.86 | 6.25 | | | | | | |
| L3 | 0.9356 | 0.9516 | 8.19 | 6.61 | | | | | | |

TABLE 5-continued

Concentration of ORF2 protein in vaccine 230-61A.
(a) data derived from peptide NVDHVGLGTAFENSK (SEQ ID NO: 4) standard curves.
(b) data derived from peptide VEFWPCSPITQGDR (SEQ ID NO: 24) standard curves.

(b)

| Sample | Ratio_T1 (846.9/1131.5) | Ratio_T2 (846.9/786.4) | Sample Conc_T1 (ug/mL) | Sample Conc_T2 (ug/mL) | average_T1 (ug/mL) | average_T2 (ug/mL) | stdev_T1 | stdev_T2 | CV-T1 | CV-T2 |
|---|---|---|---|---|---|---|---|---|---|---|
| L1 | 0.0971 | 0.0864 | 4.15 | 4.00 | 4.17 | 4.17 | 0.15 | 0.17 | 4 | 4 |
| L2 | 0.0946 | 0.0899 | 4.04 | 4.16 | | | | | | |
| L3 | 0.1016 | 0.0938 | 4.33 | 4.35 | | | | | | |

Blank and Double Blank

Blank (no ORF2, but with added AQUA peptides) and double blank (also no AQUA peptides) samples (230-64E) were prepared for the study. Blank and double blank traces were compared to the lowest point of the standard curve at 3.125 µg/mL concentration. (Chromatograms of peptide NVDHVGLGTAFENSK (SEQ ID NO:4) and VEFWPCSPITQGDR (SEQ ID NO:24) transitions not shown.) There are less than 1% of interferences for the transitions monitored.

Vaccine Serial Dilution Curves

Vaccine 261-007B-1, 261-007C-1, 261-007D-1, and 261-007F-1 series were diluted using sample 230-64E by 2, 4, 8, 16, and 32 fold. Vaccine 261-007B, 261-007C, 261-007D, and 261-007F series were diluted using sample 230-61C by 2, 4, 8, 16, and 32 fold. Each concentration point was individually processed. The extracted mass-selected MRM chromatograms for vaccine 231-007B-1 and vaccine 231-007B are not shown. A plot of the ratio of the peak area of endogenous ORF2 peptide to the peak area of AQUA peptide against relative concentration (where the starting concentration is defined as 1) was made for 261-007-1 series, peptide NVDHVGLGTAFENSK (SEQ ID NO:4); 261-007-1 series, peptide VEFWPCSPITQGDR (SEQ ID NO:24); 261-007 series, peptide NVDHVGLGTAFENSK (SEQ ID NO:4); and 261-007 series, peptide VEFWPCSPITQGDR (SEQ ID NO:24).

Based on the ELISA data done previously, the ORF2 concentration varies slightly within each set of vaccine, with F having the highest ORF2 concentration and B having the lowest ORF2 concentration. The MRM results are consistent with the ELISA data.

Discussion

Peptide ISIPFEYYR (SEQ ID NO:26)

Peptide ISIPFEYYR (SEQ ID NO:26) had the strongest signal among the three peptides chosen for quantitate the ORF2 concentration. However, it was abandoned early for the following reasons. First of all, its standard curve is significantly non-linear, showing a saturation trend. Secondly, the vaccine dilution series showed an abnormal trend, such as the 1/2 dilution point had a higher ratio than the undiluted vaccine. This behavior indicated some interaction of the peptide with a porcine serum protein.

Digestion Efficiency and Consistency

A longer version of peptide ISIPFEYYR (SEQ ID NO:26) was synthesized with stable isotope labeled isoleucine incorporated into the sequence. Its sequence is (GGGTNK[IC$^{13}$N$^{15}$]S[IC$^{13}$N$^{15}$]PFEYYRIRKVKVEF) (SEQ ID NO:28). This peptide contained two trypsin digestion sites. After complete trypsin digestion, this longer peptide is converted to [IC$^{13}$N$^{15}$]S[IC$^{13}$N$^{15}$]PFEYYR (SEQ ID NO:4). The ratio of MRM transitions of this peptide to the MRM transitions of AQUA peptide ISIPFEYY[RC$^{13}$N$^{15}$] (SEQ ID NO:26) is calculated to determine the trypsin digestion efficiency and consistency. The ratio from the standard curve series (data not shown) showed that the digestion efficiency is around 2-2.5% for this long peptide. The variation for the digestion is less than 15% across 42 data points. One possible explanation for the low digestion efficiency of this long peptide is because it may not have the perfect binding site for trypsin. Trypsin Digestion efficiency of the intact ORF2 protein can be very different and much higher than this peptide.

Summary

Two of the three tryptic peptides initially suggested by ABI MultiQuant Software (version 1.0) to be the most likely to be useful in the invention performed as expected. Surprisingly, although peptide ISIPFEYYR (SEQ ID NO:26) had the strongest signal among the three peptides chosen for quantitate the ORF2 concentration in initial experiments, it failed to have the required characteristics for quantitative analysis, perhaps due to unexpected interference with a porcine serum protein.

Example 2: Sample Preparation for MRM

SEC-MRM Procedure for Isolation of Virus-Like Particles and Trypsin Digestion for Use in MRM Invert the CHROMA SPIN Column several times to completely resuspend the gel matrix.

Remove the top cap first and then the bottom cap from the column. Save the caps. Place the bottom tip of the column gently (snugly, but not tightly) into one of the 2-ml microcentrifuge tubes provided.

Centrifuge the column in a swinging bucket rotor or in a fixed-angle rotor at 700×g for 3 min.

Discard the collected buffer from the 2-ml tube. Replace the column gently in the tube. Add 1 ml of the PBS to the gel.

Centrifuge again at 700×g for 3 min.

Empty the 2-ml collection tube and replace the column gently in the same 2-ml tube.

Add 1 ml of the PBS to the gel and centrifuge again at 700×g for 3 min.

Empty the 2-ml collection tube and replace the column gently in the same 2-ml tube. Centrifuge again at 700×g for 3 min to remove remaining PBS from the column.

Place the spin column into the second 2-ml microcentrifuge tube. Carefully and slowly apply 70 µL sample to the center of the gel bed's flat surface. Do not allow any sample to flow along the inner wall of the column.

Centrifuge at 700×g for 3 min.

The microfuge tube contains VLPs.

Transfer 10 µl VLPs to 96 wells plate.

Add 100 μl of Master solution containing 0.1% RAPIGEST® (sodium 3-[(2-methyl-2-undecyl-1,3-dioxolan-4-yl)methoxy]-1-propanesulfonate) into each wells of plate.

Add 10 μl of 0.1M DTT and vortex briefly. Seal the plate with caps and incubate at 37 degree C. for 40 min.

Add 25 μl of 0.1M IAA. Seal the plate with caps and incubate under constant vortexing at room temp for 0.5 hr (keep in the dark).

Add 15 μl of 8 μg/ml trypsin (0.8 μg/μl in final solution) and vortex briefly. Seal the plate with caps and incubate at 37 C for 16 hr.

Add 15 μl of HCl (2 M) and vortex briefly. Seal the plate with caps and incubate at 37 degree for 1 hr.

Filter extracts and inject 20 μL to HPLC and Monitor MRM transitions on AB Sciex 5000.

Immunoprecipitation (IP) Method

1. Coat a 96-position, Immulon 1B flat bottom microtiter medium binding polystyrene plate by adding 300 μL of loading buffer into each well. Incubate at RT for 10 min. Discard the loading buffer and let the plate dry.
2. Dilute all the samples as instructed here. Take 10 μL of samples into loBind eppendoff tubes. Add 490 μL of loading buffer. Mix well by vortexing.
3. Take 50 μL aliquot of the diluted samples into each well of the pre-coated 96-position plate.
4. Add 10 μL of polyclonal antibodies (pAb) (0.7 mg/mL in loading buffer) to each well.
5. Incubate at RT with vortex at medium speed for 2 h.
Add 100 μL of protein G beads (6 mg/mL in loading buffer) to each well.
7. Incubate at RT with vortex at medium speed for 2 h.
8. Wash with washing buffer for four times with vortexing between each wash.
9. Add 25 μL of RAPIGEST® (sodium 3-[(2-methyl-2-undecyl-1,3-dioxolan-4-yl)methoxy]-1-propanesulfonate) solution to each well.
10. Add 10 μL of working standard solution (1 μg/mL in 50 mM ammonium bicarbonate) to each well.
11. Add 10 μL of 0.1 M DTT to each well.
12. Incubate at 60° C. with vortex at speed of 650 RPM for 1 h using the Thermomixer.
13. Add 25 μL of 0.1 M IAA to each well.
14. Incubate at RT in yellow room with vortex at medium speed for ½ h.
15. Add 10 μL of trypsin solution (0.5 mg/mL) to each well.
16. Incubate at 37° C. overnight (16 h) with vortex at medium speed.
17. Add 10 μL of 3 M HCl to each well.
18. Incubate at 37° C. with vortex at medium speed for ½ h.
19. Transfer all the samples to a multiscreen HST filter plate (the filter plate is taped together with a 96-position 2.0 mL, conical well plate). Centrifuge at 3000 RPM for 3 min.

Autosampler Method Using an Automated Laboratory Sample Handling Platform to Inject Samples into HPLC Column

| Autosampler: | CTC Analytics LCPAL |
| --- | --- |
| Cycle | Analyst LC-Inj |
| Syringe | 100 μL |
| Sample Volume | 5 μL |
| Air Volume | 0 μL |
| Pre Clean with solvent 1 ( ) | 0 μL |
| Pre Clean with Solvent 2 ( ) | 0 μL |
| Pre Clean with Sample ( ) | 0 μL |
| Fill speed | 30 μL/s |
| Fill strokes | 0 |
| Inject to | LC Vlv1 |
| Inject speed | 30 μL/s |
| Pre Inj Del | 500 ms |
| Pst Inj Del | 500 ms |
| Pst Cln Slv1 | 1 |
| Pst Cln Slv2 | 1 |
| Vlv Cln Slv1 | 1 |
| Vlv Cln Slv2 | 1 |
| Replicate Count ( ) | 1 |
| Analysis Time (s) | 0 |
| Cooler Temperature: | 6 |

Chromatography

LC Pump: HP 1100 Series or 1200 Series

Analytical Column: Waters BIOSUITE C18®, Product No. 00D-4439-B0

Column Temperature: 40° C.

Pump Program: Gradient

Mobile Phase A1: 99:1:0.5 Water/Isopropanol Alcohol/Formic Acid

Mobile Phase B1: 70:24:5:1:0.5 Acetonitrile/Methanol/Water/Isopropanol Alcohol/Formic Acid Flow Rate: 0.3 mL/min Injector Loop: 20 μL Injection Volume: 25 μL LC Pressure: 40 to 180 bar Autosampler Wash 1: 70:20:5:5 Acetonitrile/Methanol/Isopropanol Alcohol/Water Autosampler Wash 2: 10:90 Acetonitrile/Water Approximate Run 7 min Time:

Analytical Pump Program—Step Table 1:

| Step | Total Time (min) | Flow Rate (μL/min) | Composition A (%) | B (%) |
| --- | --- | --- | --- | --- |
| 0 | 0 | 500 | 92 | 8 |
| 1 | 1 | 300 | 92 | 8 |
| 2 | 1.1 | 300 | 74 | 26 |
| 3 | 4.5 | 300 | 63 | 37 |
| 4 | 5.0 | 500 | 30 | 70 |
| 5 | 5.5 | 500 | 30 | 70 |
| 6 | 6.0 | 500 | 92 | 8 |
| 7 | 7.0 | 500 | 92 | 8 |

Make-Up Pump Program—Step Table 2:

| Step | Total Time (min) | Flow Rate (μL/min) | Composition A (%) | B (%) |
| --- | --- | --- | --- | --- |
| 0 | 0 | 200 | 50 | 50 |
| 1 | 7 | 200 | 50 | 50 |

Valve Program

| Total Time (min) | Position | Comments |
| --- | --- | --- |
| Initial | Left | Load Sample/Desalting |
| 1.2 | Right | Transfer/Elute |
| 5.5 | Left | Regeneration |

Mass Spectrometry

| | |
| --- | --- |
| Mass Spectrometer: | Sciex API 5000, Triple quadrupole LC/MS/MS |
| Ionization Mode: | Turbo IonSpray |
| CAD, CUR, NEB, AUX Gas: | Nitrogen |
| Resolution Q1: | Unit |
| Resolution Q3: | Unit |
| Ion Energy 1 (1E1) | 1 |
| Ion Energy 3 (1E3) | 0.2 |
| Quantitation: | Based on peak area |
| Calibration: | PPGs |
| Ion Source Temp: | 550° C. |
| IonSpray Voltage | 5000 V |
| Electron Multiplier (CEM): | 2000 V |
| Collision Gas Flow (CAD): | 12 |
| Curtain Gas Flow (CUR): | 20 |
| Nebulizer Gas Flow (NEB/GS1): | 60 |
| Turbo IonSpray Gas (AUX/GS2): | 50 |
| Deflector Potential (DF): | 100 |
| Pause Time: | 56.3 ms |
| Acquisition Time: | 7 min |
| Processing Model: | Intelliquan |

The following electrospray ionization source parameters were used: dwell time, 50 ms for all MRM transitions; ion-spray voltage, 5000 V; ion source temperature, 550° C.; curtain gas (CUR), 20. DP: declustering potential. CE: collision energy. CXP: collision cell exit potential.

| Analyte | ~$t_R$ (min) | Dwell Time (ms) | Q1 m/z | Q3 m/z | DP | CE | CXP | EP |
| --- | --- | --- | --- | --- | --- | --- | --- | --- |
| VEF | 4.0 | 50 | 846.9 | 1131.5 | 60 | 38 | 15 | 10 |
| IS | 4.0 | 50 | 851.9 | 1141.5 | 60 | 38 | 15 | 10 |
| ISI | 3.8 | 50 | 594.3 | 874.4 | 80 | 42 | 15 | 10 |
| NVD | 2.8 | 50 | 794.4 | 1023.5 | 80 | 36 | 15 | 10 |

Size Exclusion Chromatography (SEC)-MRM

The use of SEC ensures that only VLP or CLP is present in a sample to be measured, as only an intact VLP or CLP structure will pass through into the void fraction. SEC-MRM allows the separation of VLP from a complex matrix with high levels of non-relevant, extraneous proteins. This method is antibody-free. If there is the possibility of a batch of antigen to contain both intact VLP and degraded VLP, the addition of the SEC step ensures that only intact VLP (i.e., true VLP) will be measured in the MRM portion of the assay.

Example 3: Quantitation Differentiation of PCV2a and PCV2b Using IP-MRM on Non-Enveloped, PCV2 ORF2 VLP PCV2a and PCV2b are antigenic subtypes of antigenically similar, but not identical VLPs. Similarly, the PCV2a ORF2 and PCV2b ORF2 VLP subtypes are antigenically similar, but are not identical at the amino acid level. The desired PCV2 ORF2 vaccine will contain a mixture of VLPs comprised of both PCV2a ORF2 and PCV2b ORF2 subtypes.

Typically, an ELISA method would be used to determine the relative antigen content (RAC) or relative potency (RP) of the two different PCV2 ORF2 subtypes in a vaccine. However, an ELISA capable of differentiating the inclusion levels of PCV2a and PCV2b would require two different MAb (one MAb that reacts only to PCV2a, and the other MAb reacting only to PCV2b). But, the generation of two distinct MAbs that are able to differentiate between the two antigenically similar PCV2a and PCV2b VLP would be a very difficult, possibly impossible, task.

IP-MRM allows the use of polyclonal antibodies to bind both PCV2a and PCV2b, followed by the subsequent differentiation and quantitation of the amounts of PCV2a and PCV2b by MRM.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the following claims.

What is claimed is:

1. A method of quantifying the presence of one or more porcine circovirus type 2 (PCV2) viral proteins forming a virus like particle in a sample, the method comprising:

a) adding a known quantity of one or more stable-isotope-labeled signature peptides specific to the one or more PCV2 viral proteins in the sample, wherein the one or more stable-isotope-labeled signature peptides are selected from the group consisting of:

i)
   (SEQ ID NO: 14)
   ANALTYDPYVNYSSR;

ii)
   (SEQ ID NO: 15)
   HTITQPFSYHSR;

iii)
   (SEQ ID NO: 18)
   LQTTGNVDHVGLGTAFENSIYDQDYNIR;

iv)
   (SEQ ID NO: 19)
   ITMYVQFR;

v)
   (SEQ ID NO: 22)
   YFTPK PVLDR; and xviii)
   (SEQ ID NO: 23)
   EFNLK DPPLNPK;

b) digesting the sample with a protease;
   c) running mass-spectroscopic analyses of the sample; and
   d) determining an amount of the one or more PCV2 viral proteins in the sample, wherein the one or more PCV2 viral proteins are capable of forming a virus like particle and/or wherein the sample comprises virus like particles composed of a plurality of the one or more PCV2 viral proteins comprising PCV subtype 2a (PCV2a) open reading frame 2(ORF2) and/or PCV subtype 2b (PCV2b) ORF2; wherein the sample is removed from one of: an animal material selected from a body fluid and a tissue, a preparation of the animal material, and a vaccine preparation.

2. The method of claim 1, wherein determining the amount of the one or more PCV2 viral proteins in the sample comprises comparing one or more signals resulting from the mass-spectroscopic analyses of the sample, wherein a first signal from each of the one or more stable-isotope-labeled signature peptides is compared with a second signal from each of the one or more peptides produced by the protease digestion of the one or more PCV2 viral proteins in the sample, wherein each amino acid sequence of the one or more signature peptides corresponds to an amino acid sequence of one peptide produced by the protease digestion of the one or more PCV2 viral proteins in the sample.

3. The method of claim 1, wherein the signature peptides are preselected by determining that they are specific to the protease digest of the viral protein to be quantified and/or that they are specifically absent from the protease digest of the sample in the absence of the viral protein.

4. The method of claim 1, further comprising:
e) determining the amount of viral protein in the sample by comparing the results of the sample mass-spectroscopic analysis with a calibration standard curve; and/or
f) running mass-spectroscopic analyses of standards containing known amounts of labeled and/or unlabeled signature peptides; and determining the amount of viral protein in the sample by comparing the results of the sample mass-spectroscopic analysis with the results of the standards, wherein the calibration standard curve is generated with the results of the standards and compared with the results of the sample mass-spectroscopic analysis.

5. The method of claim 1, wherein the preparation contains agents which bind to said viral protein.

6. The method of claim 1, further comprising, before protease digestion, immunopurifying the viral protein.

7. The method of claim 6, wherein the immunopurification comprises:
i) contacting the viral proteins with antibodies that bind specifically to the viral proteins that correspond to the sequence in the signature peptides, wherein said antibodies are fixed to a substrate, and whereby substrate/antibody-protein complexes are formed;
ii) washing the substrate with an eluent that does not cause the antibody-protein complexes to dissociate;
iii) contacting the antibody-protein complexes with a protease; and iv) eluting the peptides generated by the protease digest with a eluent that causes the antibody-peptide complexes to dissociate;
wherein the peptides obtained thereby are used in subsequent steps a)-d).

8. The method of claim 1, further comprising, before protease digestion, passing the preparation over a size-exclusion chromatographic column and selecting the fractions eluted from the column containing viral protein from fractions containing other compounds in the preparation, on the basis of molecular size.

9. The method of claim 8, wherein the fractions containing intact virus-like particles (VLPs) are selected.

10. The method of claim 1, further comprising, after protease digestion, immunopurifying the viral protein digest.

11. The method of claim 1, wherein at least two stable-isotope-labeled signature peptides are used, and wherein a first signature peptide is used for quantitation of the viral peptide in the preparation and a second signature peptide is used for qualitative determination of the stability of the peptide in the preparation.

12. The method of claim 11, wherein the qualitative determination measures whether degraded viral protein is present in the sample.

13. The method of claim 1, wherein the running mass-spectroscopic analyses includes:
a. selecting an ion of interest related to the signature peptide;
b. filtering a plurality of ions generated by an ionization of particles within the sample; and
c. analyzing fragment ions corresponding to the ion of interest.

14. The method of claim 1, wherein the running of the mass-spectroscopic analyses comprises:
a. ionizing the sample;
b. separating a plurality of ions according to their mass-to-charge ratios; and
c. detecting at least one ion corresponding to the viral protein.

15. The method of claim 1, wherein the protease is selected from the group consisting of trypsin, chymotrypsin, pepsin, thrombin, papain, bromelain, thermolysin, subtilisin, Factor Xa, *Staphylococcus aureus* protease, carboxypeptidase A, and combinations thereof.

16. The method of claim 1, wherein the animal material is selected from blood, blood serum, blood plasma, urine, colostrum, tissue sections, and tissue biopsies.

17. A method of diagnosis or monitoring of a virus infection comprising the method of claim 1.

18. The method of claim 17, wherein the virus infection is an infection with PCV2 wherein the PCV2 comprises PCV2a and/or PCV2b, and/or wherein the animal is a pig.

* * * * *

SEQUENCE LISTING

<160> NUMBER OF SEQ ID NOS: 33

<210> SEQ ID NO 1
<211> LENGTH: 233
<212> TYPE: PRT
<213> ORGANISM: Porcine circovirus

<400> SEQUENCE: 1

Met Thr Tyr Pro Arg Arg Arg Tyr Arg Arg Arg His Arg Pro Arg
1               5                   10                  15

Ser His Leu Gly Gln Ile Leu Arg Arg Pro Trp Leu Val His Pro
            20                  25                  30

Arg His Arg Tyr Arg Trp Arg Arg Lys Asn Gly Ile Phe Asn Thr Arg

```
                35                  40                  45
Leu Ser Arg Thr Phe Gly Tyr Thr Val Lys Ala Thr Thr Val Thr Thr
 50                  55                  60

Pro Ser Trp Ala Val Asp Met Met Arg Phe Asn Ile Asp Asp Phe Val
 65                  70                  75                  80

Pro Pro Gly Gly Gly Thr Asn Lys Ile Ser Ile Pro Phe Glu Tyr Tyr
                    85                  90                  95

Arg Ile Arg Lys Val Lys Val Glu Phe Trp Pro Cys Ser Pro Ile Thr
                100                 105                 110

Gln Gly Asp Arg Gly Val Gly Ser Thr Ala Val Ile Leu Asp Asp Asn
                115                 120                 125

Phe Val Thr Lys Ala Thr Ala Leu Thr Tyr Asp Pro Tyr Val Asn Tyr
                130                 135                 140

Ser Ser Arg His Thr Ile Pro Gln Pro Phe Ser Tyr His Ser Arg Tyr
145                 150                 155                 160

Phe Thr Pro Lys Pro Val Leu Asp Ser Thr Ile Asp Tyr Phe Gln Pro
                165                 170                 175

Asn Asn Lys Arg Asn Gln Leu Trp Leu Arg Leu Gln Thr Ser Arg Asn
                180                 185                 190

Val Asp His Val Gly Leu Gly Thr Ala Phe Glu Asn Ser Lys Tyr Asp
                195                 200                 205

Gln Asp Tyr Asn Ile Arg Val Thr Met Tyr Val Gln Phe Arg Glu Phe
                210                 215                 220

Asn Leu Lys Asp Pro Pro Leu Glu Pro
225                 230

<210> SEQ ID NO 2
<211> LENGTH: 233
<212> TYPE: PRT
<213> ORGANISM: Porcine circovirus

<400> SEQUENCE: 2

Met Thr Tyr Pro Arg Arg Arg Tyr Arg Arg Arg His Arg Pro Arg
  1               5                  10                  15

Ser His Leu Gly Gln Ile Leu Arg Arg Arg Pro Trp Leu Val His Pro
                 20                  25                  30

Arg His Arg Tyr Arg Trp Arg Arg Lys Asn Gly Ile Phe Asn Thr Arg
                 35                  40                  45

Leu Ser Arg Thr Phe Gly Tyr Thr Ile Lys Arg Thr Thr Val Arg Thr
 50                  55                  60

Pro Ser Trp Ala Val Asp Met Met Arg Phe Asn Ile Asn Asp Phe Leu
 65                  70                  75                  80

Pro Pro Gly Gly Gly Ser Asn Pro Arg Ser Val Pro Phe Glu Tyr Tyr
                    85                  90                  95

Arg Ile Arg Lys Val Lys Val Glu Phe Trp Pro Cys Ser Pro Ile Thr
                100                 105                 110

Gln Gly Asp Arg Gly Val Gly Ser Ser Ala Val Ile Leu Asp Asp Asn
                115                 120                 125

Phe Val Pro Lys Ala Thr Ala Leu Thr Tyr Asp Pro Tyr Val Asn Tyr
                130                 135                 140

Ser Ser Arg His Thr Ile Thr Gln Pro Phe Ser Tyr His Ser Arg Tyr
145                 150                 155                 160

Phe Thr Pro Lys Pro Val Leu Asp Gly Thr Ile Asp Tyr Phe Gln Pro
                165                 170                 175
```

```
Asn Asn Lys Arg Asn Gln Leu Trp Leu Arg Leu Gln Thr Ala Gly Asn
            180                 185                 190

Val Asp His Val Gly Leu Gly Thr Ala Phe Glu Asn Ser Ile Tyr Asp
        195                 200                 205

Gln Glu Tyr Asn Ile Arg Val Thr Met Tyr Val Gln Phe Arg Glu Phe
    210                 215                 220

Asn Leu Lys Asp Pro Pro Leu Asn Pro
225                 230

<210> SEQ ID NO 3
<211> LENGTH: 234
<212> TYPE: PRT
<213> ORGANISM: Porcine circovirus

<400> SEQUENCE: 3

Met Thr Tyr Pro Arg Arg Arg Phe Arg Arg Arg Arg His Arg Pro Arg
1               5                   10                  15

Ser His Leu Gly Gln Ile Leu Arg Arg Arg Pro Trp Leu Val His Pro
            20                  25                  30

Arg His Arg Tyr Arg Trp Arg Arg Lys Asn Gly Ile Phe Asn Thr Arg
        35                  40                  45

Leu Ser Arg Thr Ile Gly Tyr Thr Val Lys Lys Thr Thr Val Thr Thr
    50                  55                  60

Pro Ser Trp Asn Val Asp Met Met Arg Phe Asn Ile Asn Asp Phe Leu
65                  70                  75                  80

Pro Pro Gly Gly Gly Ser Asn Pro Leu Thr Val Pro Phe Glu Tyr Tyr
                85                  90                  95

Arg Ile Arg Lys Val Lys Val Glu Phe Trp Pro Cys Ser Pro Ile Thr
            100                 105                 110

Gln Gly Asp Arg Gly Val Gly Ser Thr Ala Val Ile Leu Asp Asp Asn
        115                 120                 125

Phe Val Thr Lys Ala Asn Ala Leu Thr Tyr Asp Pro Tyr Val Asn Tyr
    130                 135                 140

Ser Ser Arg His Thr Ile Thr Gln Pro Phe Ser Tyr His Ser Arg Tyr
145                 150                 155                 160

Phe Thr Pro Lys Pro Val Leu Asp Arg Thr Ile Asp Tyr Phe Gln Pro
                165                 170                 175

Asn Asn Lys Arg Asn Gln Leu Trp Leu Arg Leu Gln Thr Thr Gly Asn
            180                 185                 190

Val Asp His Val Gly Leu Gly Thr Ala Phe Glu Asn Ser Ile Tyr Asp
        195                 200                 205

Gln Asp Tyr Asn Ile Arg Ile Thr Met Tyr Val Gln Phe Arg Glu Phe
    210                 215                 220

Asn Leu Lys Asp Pro Pro Leu Asn Pro Lys
225                 230

<210> SEQ ID NO 4
<211> LENGTH: 15
<212> TYPE: PRT
<213> ORGANISM: Artificial Sequence
<220> FEATURE:
<223> OTHER INFORMATION: Description of Artificial Sequence: Synthetic
      mass-labeled peptide derived from the ORF2 protein of porcine
      circovirus (PCV)
<220> FEATURE:
<221> NAME/KEY: MOD_RES
<222> LOCATION: (15)..(15)
<223> OTHER INFORMATION: Preferably C

```
<400> SEQUENCE: 4

Asn Val Asp His Val Gly Leu Gly Thr Ala Phe Glu Asn Ser Lys
1               5                   10                  15

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
      mass-labeled peptide derived from the ORF2 protein of porcine
      circovirus (PCV)
<220> FEATURE:
<221> NAME/KEY: MOD_RES
<222> LOCATION: (7)..(7)
<223> OTHER INFORMATION: Preferably C13 and N15 isotope labeled

<400> SEQUENCE: 5

Thr Phe Gly Tyr Thr Val Lys
1               5

<210> SEQ ID NO 6
<211> LENGTH: 15
<212> TYPE: PRT
<213> ORGANISM: Artificial Sequence
<220> FEATURE:
<223> OTHER INFORMATION: Description of Artificial Sequence: Synthetic
      mass-labeled peptide derived from the ORF2 protein of porcine
      circovirus (PCV)
<220> FEATURE:
<221> NAME/KEY: MOD_RES
<222> LOCATION: (15)..(15)
<223> OTHER INFORMATION: Preferably C13 and N15 isotope labeled

<400> SEQUENCE: 6

Ala Thr Thr Val Thr Thr Pro Ser Trp Ala Val Asp Met Met Arg
1               5                   10                  15

<210> SEQ ID NO 7
<211> LENGTH: 24
<212> TYPE: PRT
<213> ORGANISM: Artificial Sequence
<220> FEATURE:
<223> OTHER INFORMATION: Description of Artificial Sequence: Synthetic
      mass-labeled peptide derived from the ORF2 protein of porcine
      circovirus (PCV)
<220> FEATURE:
<221> NAME/KEY: MOD_RES
<222> LOCATION: (24)..(24)
<223> OTHER INFORMATION: Preferably C13 and N15 isotope labeled

<400> SEQUENCE: 7

Phe Asn Ile Asp Asp Phe Val Pro Pro Gly Gly Gly Thr Asn Lys Ile
1               5                   10                  15

Ser Ile Pro Phe Glu Tyr Tyr Arg
            20

<210> SEQ ID NO 8
<211> LENGTH: 15
<212> TYPE: PRT
<213> ORGANISM: Artificial Sequence
<220> FEATURE:
<223> OTHER INFORMATION: Description of Artificial Sequence: Synthetic
      mass-labeled peptide derived from the ORF2 protein of porcine
      circovirus (PCV)
<220> FEATURE:
<221> NAME/KEY: MOD_RES
<222> LOCATION: (15)..(15)
<223> OTHER INFORMATION: Preferably C13 and N15 isotope labeled
```

-continued

```
<400> SEQUENCE: 8

Ala Thr Ala Leu Thr Tyr Asp Pro Tyr Val Asn Tyr Ser Ser Arg
1               5                   10                  15

<210> SEQ ID NO 9
<211> LENGTH: 12
<212> TYPE: PRT
<213> ORGANISM: Artificial Sequence
<220> FEATURE:
<223> OTHER INFORMATION: Description of Artificial Sequence: Synthetic
      mass-labeled peptide derived from the ORF2 protein of porcine
      circovirus (PCV)
<220> FEATURE:
<221> NAME/KEY: MOD_RES
<222> LOCATION: (12)..(12)
<223> OTHER INFORMATION: Preferably C13 and N15 isotope labeled

<400> SEQUENCE: 9

His Thr Ile Pro Gln Pro Phe Ser Tyr His Ser Arg
1               5                   10

<210> SEQ ID NO 10
<211> LENGTH: 20
<212> TYPE: PRT
<213> ORGANISM: Artificial Sequence
<220> FEATURE:
<223> OTHER INFORMATION: Description of Artificial Sequence: Synthetic
      mass-labeled peptide derived from the ORF2 protein of porcine
      circovirus (PCV)
<220> FEATURE:
<221> NAME/KEY: MOD_RES
<222> LOCATION: (20)..(20)
<223> OTHER INFORMATION: Preferably C13 and N15 isotope labeled

<400> SEQUENCE: 10

Tyr Phe Thr Pro Lys Pro Val Leu Asp Ser Thr Ile Asp Tyr Phe Gln
1               5                   10                  15

Pro Asn Asn Lys
            20

<210> SEQ ID NO 11
<211> LENGTH: 8
<212> TYPE: PRT
<213> ORGANISM: Artificial Sequence
<220> FEATURE:
<223> OTHER INFORMATION: Description of Artificial Sequence: Synthetic
      mass-labeled peptide derived from the ORF2 protein of porcine
      circovirus (PCV)
<220> FEATURE:
<221> NAME/KEY: MOD_RES
<222> LOCATION: (8)..(8)
<223> OTHER INFORMATION: Preferably C13 and N15 isotope labeled

<400> SEQUENCE: 11

Val Thr Met Tyr Val Gln Phe Arg
1               5

<210> SEQ ID NO 12
<211> LENGTH: 15
<212> TYPE: PRT
<213> ORGANISM: Artificial Sequence
<220> FEATURE:
<223> OTHER INFORMATION: Description of Artificial Sequence: Synthetic
      mass-labeled peptide derived from the ORF2 protein of porcine
      circovirus (PCV)
<220> FEATURE:
<221> NAME/KEY: MOD_RES
<222> LOCATION: (15)..(15)
<223> OTHER INFORMATION: Preferably C13 and N15 isotope labeled
```

-continued

```
<400> SEQUENCE: 12

Met Thr Thr Val Thr Thr Pro Ser Trp Asn Val Asp Met Met Arg
1               5                   10                  15

<210> SEQ ID NO 13
<211> LENGTH: 24
<212> TYPE: PRT
<213> ORGANISM: Artificial Sequence
<220> FEATURE:
<223> OTHER INFORMATION: Description of Artificial Sequence: Synthetic
      mass-labeled peptide derived from the ORF2 protein of porcine
      circovirus (PCV)
<220> FEATURE:
<221> NAME/KEY: MOD_RES
<222> LOCATION: (24)..(24)
<223> OTHER INFORMATION: Preferably C13 and N15 isotope labeled

<400> SEQUENCE: 13

Phe Asn Ile Asn Asp Phe Leu Pro Pro Gly Gly Gly Ser Asn Pro Leu
1               5                   10                  15

Thr Val Pro Phe Glu Tyr Tyr Arg
            20

<210> SEQ ID NO 14
<211> LENGTH: 15
<212> TYPE: PRT
<213> ORGANISM: Artificial Sequence
<220> FEATURE:
<223> OTHER INFORMATION: Description of Artificial Sequence: Synthetic
      mass-labeled peptide derived from the ORF2 protein of porcine
      circovirus (PCV)
<220> FEATURE:
<221> NAME/KEY: MOD_RES
<222> LOCATION: (15)..(15)
<223> OTHER INFORMATION: Preferably C13 and N15 isotope labeled

<400> SEQUENCE: 14

Ala Asn Ala Leu Thr Tyr Asp Pro Tyr Val Asn Tyr Ser Ser Arg
1               5                   10                  15

<210> SEQ ID NO 15
<211> LENGTH: 12
<212> TYPE: PRT
<213> ORGANISM: Artificial Sequence
<220> FEATURE:
<223> OTHER INFORMATION: Description of Artificial Sequence: Synthetic
      mass-labeled peptide derived from the ORF2 protein of porcine
      circovirus (PCV)
<220> FEATURE:
<221> NAME/KEY: MOD_RES
<222> LOCATION: (12)..(12)
<223> OTHER INFORMATION: Preferably C13 and N15 isotope labeled

<400> SEQUENCE: 15

His Thr Ile Thr Gln Pro Phe Ser Tyr His Ser Arg
1               5                   10

<210> SEQ ID NO 16
<211> LENGTH: 5
<212> TYPE: PRT
<213> ORGANISM: Artificial Sequence
<220> FEATURE:
<223> OTHER INFORMATION: Description of Artificial Sequence: Synthetic
      mass-labeled peptide derived from the ORF2 protein of porcine
      circovirus (PCV)
<220> FEATURE:
<221> NAME/KEY: MOD_RES
<222> LOCATION: (5)..(5)
<223> OTHER INFORMATION: Preferably C13 and N15 isotope labeled
```

```
<400> SEQUENCE: 16

Tyr Phe Thr Pro Lys
1               5

<210> SEQ ID NO 17
<211> LENGTH: 5
<212> TYPE: PRT
<213> ORGANISM: Artificial Sequence
<220> FEATURE:
<223> OTHER INFORMATION: Description of Artificial Sequence: Synthetic
      mass-labeled peptide derived from the ORF2 protein of porcine
      circovirus (PCV)
<220> FEATURE:
<221> NAME/KEY: MOD_RES
<222> LOCATION: (5)..(5)
<223> OTHER INFORMATION: Preferably C13 and N15 isotope labeled

<400> SEQUENCE: 17

Pro Val Leu Asp Arg
1               5

<210> SEQ ID NO 18
<211> LENGTH: 28
<212> TYPE: PRT
<213> ORGANISM: Artificial Sequence
<220> FEATURE:
<223> OTHER INFORMATION: Description of Artificial Sequence: Synthetic
      mass-labeled peptide derived from the ORF2 protein of porcine
      circovirus (PCV)
<220> FEATURE:
<221> NAME/KEY: MOD_RES
<222> LOCATION: (28)..(28)
<223> OTHER INFORMATION: Preferably C13 and N15 isotope labeled

<400> SEQUENCE: 18

Leu Gln Thr Thr Gly Asn Val Asp His Val Gly Leu Gly Thr Ala Phe
1               5                   10                  15

Glu Asn Ser Ile Tyr Asp Gln Asp Tyr Asn Ile Arg
            20                  25

<210> SEQ ID NO 19
<211> LENGTH: 8
<212> TYPE: PRT
<213> ORGANISM: Artificial Sequence
<220> FEATURE:
<223> OTHER INFORMATION: Description of Artificial Sequence: Synthetic
      mass-labeled peptide derived from the ORF2 protein of porcine
      circovirus (PCV)
<220> FEATURE:
<221> NAME/KEY: MOD_RES
<222> LOCATION: (8)..(8)
<223> OTHER INFORMATION: Preferably C13 and N15 isotope labeled

<400> SEQUENCE: 19

Ile Thr Met Tyr Val Gln Phe Arg
1               5

<210> SEQ ID NO 20
<211> LENGTH: 5
<212> TYPE: PRT
<213> ORGANISM: Artificial Sequence
<220> FEATURE:
<223> OTHER INFORMATION: Description of Artificial Sequence: Synthetic
      mass-labeled peptide derived from the ORF2 protein of porcine
      circovirus (PCV)
<220> FEATURE:
<221> NAME/KEY: MOD_RES
<222> LOCATION: (5)..(5)
<223> OTHER INFORMATION: Preferably C13 and N15 isotope labeled
```

<400> SEQUENCE: 20

Glu Phe Asn Leu Lys
1               5

<210> SEQ ID NO 21
<211> LENGTH: 7
<212> TYPE: PRT
<213> ORGANISM: Artificial Sequence
<220> FEATURE:
<223> OTHER INFORMATION: Description of Artificial Sequence: Synthetic
      mass-labeled peptide derived from the ORF2 protein of porcine
      circovirus (PCV)
<220> FEATURE:
<221> NAME/KEY: MOD_RES
<222> LOCATION: (7)..(7)
<223> OTHER INFORMATION: Preferably C13 and N15 isotope labeled

<400> SEQUENCE: 21

Asp Pro Pro Leu Asn Pro Lys
1               5

<210> SEQ ID NO 22
<211> LENGTH: 10
<212> TYPE: PRT
<213> ORGANISM: Artificial Sequence
<220> FEATURE:
<223> OTHER INFORMATION: Description of Artificial Sequence: Synthetic
      mass-labeled peptide derived from the ORF2 protein of porcine
      circovirus (PCV)
<220> FEATURE:
<221> NAME/KEY: MOD_RES
<222> LOCATION: (10)..(10)
<223> OTHER INFORMATION: Preferably C13 and N15 isotope labeled

<400> SEQUENCE: 22

Tyr Phe Thr Pro Lys Pro Val Leu Asp Arg
1               5                   10

<210> SEQ ID NO 23
<211> LENGTH: 12
<212> TYPE: PRT
<213> ORGANISM: Artificial Sequence
<220> FEATURE:
<223> OTHER INFORMATION: Description of Artificial Sequence: Synthetic
      mass-labeled peptide derived from the ORF2 protein of porcine
      circovirus (PCV)
<220> FEATURE:
<221> NAME/KEY: MOD_RES
<222> LOCATION: (12)..(12)
<223> OTHER INFORMATION: Preferably C13 and N15 isotope labeled

<400> SEQUENCE: 23

Glu Phe Asn Leu Lys Asp Pro Pro Leu Asn Pro Lys
1               5                   10

<210> SEQ ID NO 24
<211> LENGTH: 14
<212> TYPE: PRT
<213> ORGANISM: Artificial Sequence
<220> FEATURE:
<223> OTHER INFORMATION: Description of Artificial Sequence: Synthetic
      mass-labeled peptide derived from the ORF2 protein of porcine
      circovirus (PCV)
<220> FEATURE:
<221> NAME/KEY: MOD_RES
<222> LOCATION: (14)..(14)
<223> OTHER INFORMATION: Preferably C13 and N15 isotope labeled

<400> SEQUENCE: 24

Val Glu Phe Trp Pro Cys Ser Pro Ile Thr Gln Gly Asp Arg

<210> SEQ ID NO 25
<211> LENGTH: 16
<212> TYPE: PRT
<213> ORGANISM: Artificial Sequence
<220> FEATURE:
<223> OTHER INFORMATION: Description of Artificial Sequence: Synthetic
      mass-labeled peptide derived from the ORF2 protein of porcine
      circovirus (PCV)
<220> FEATURE:
<221> NAME/KEY: MOD_RES
<222> LOCATION: (16)..(16)
<223> OTHER INFORMATION: Preferably C13 and N15 isotope labeled

<400> SEQUENCE: 25

Gly Val Gly Ser Thr Ala Val Ile Leu Asp Asp Asn Phe Val Thr Lys
1               5                   10                  15

<210> SEQ ID NO 26
<211> LENGTH: 9
<212> TYPE: PRT
<213> ORGANISM: Artificial Sequence
<220> FEATURE:
<223> OTHER INFORMATION: Description of Artificial Sequence: Synthetic
      mass-labeled peptide derived from the ORF2 protein of porcine
      circovirus (PCV)
<220> FEATURE:
<221> NAME/KEY: MOD_RES
<222> LOCATION: (9)..(9)
<223> OTHER INFORMATION: Preferably C13 and N15 isotope labeled

<400> SEQUENCE: 26

Ile Ser Ile Pro Phe Glu Tyr Tyr Arg
1               5

<210> SEQ ID NO 27
<211> LENGTH: 8
<212> TYPE: PRT
<213> ORGANISM: Artificial Sequence
<220> FEATURE:
<223> OTHER INFORMATION: Description of Artificial Sequence: Synthetic
      mass-labeled peptide derived from the ORF2 protein of porcine
      circovirus (PCV)
<220> FEATURE:
<221> NAME/KEY: MOD_RES
<222> LOCATION: (8)..(8)
<223> OTHER INFORMATION: Preferably C13 and N15 isotope labeled

<400> SEQUENCE: 27

Ser Val Pro Phe Glu Tyr Tyr Arg
1               5

<210> SEQ ID NO 28
<211> LENGTH: 23
<212> TYPE: PRT
<213> ORGANISM: Artificial Sequence
<220> FEATURE:
<223> OTHER INFORMATION: Description of Artificial Sequence: Synthetic
      mass-labeled peptide derived from the ORF2 protein of porcine
      circovirus (PCV)
<220> FEATURE:
<221> NAME/KEY: MOD_RES
<222> LOCATION: (7)..(7)
<223> OTHER INFORMATION: Preferably C13 and N15 isotope labeled
<220> FEATURE:
<221> NAME/KEY: MOD_RES
<222> LOCATION: (9)..(9)
<223> OTHER INFORMATION: Preferably C13 and N15 isotope labeled

<400> SEQUENCE: 28

```
Gly Gly Gly Thr Asn Lys Ile Ser Ile Pro Phe Glu Tyr Tyr Arg Ile
1               5                   10                  15

Arg Lys Val Lys Val Glu Phe
            20

<210> SEQ ID NO 29
<211> LENGTH: 12
<212> TYPE: PRT
<213> ORGANISM: Artificial Sequence
<220> FEATURE:
<223> OTHER INFORMATION: Description of Artificial Sequence: Synthetic
      mass-labeled peptide derived from the ORF2 protein of porcine
      circovirus (PCV)
<220> FEATURE:
<221> NAME/KEY: MOD_RES
<222> LOCATION: (12)..(12)
<223> OTHER INFORMATION: Preferably C13 and N15 isotope labeled

<400> SEQUENCE: 29

Ser Val Gly Leu Gly Thr Ala Phe Glu Asn Ser Lys
1               5                   10

<210> SEQ ID NO 30
<211> LENGTH: 233
<212> TYPE: PRT
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: MOD_RES
<222> LOCATION: (57)..(57)
<223> OTHER INFORMATION: Val or Ile
<220> FEATURE:
<221> NAME/KEY: MOD_RES
<222> LOCATION: (59)..(59)
<223> OTHER INFORMATION: Ala or Arg
<220> FEATURE:
<221> NAME/KEY: MOD_RES
<222> LOCATION: (63)..(63)
<223> OTHER INFORMATION: Thr or Arg
<220> FEATURE:
<221> NAME/KEY: MOD_RES
<222> LOCATION: (77)..(77)
<223> OTHER INFORMATION: Asp or Asn
<220> FEATURE:
<221> NAME/KEY: MOD_RES
<222> LOCATION: (80)..(80)
<223> OTHER INFORMATION: Val or Leu
<220> FEATURE:
<221> NAME/KEY: MOD_RES
<222> LOCATION: (86)..(86)
<223> OTHER INFORMATION: Thr or Ser
<220> FEATURE:
<221> NAME/KEY: MOD_RES
<222> LOCATION: (88)..(88)
<223> OTHER INFORMATION: Lys or Pro
<220> FEATURE:
<221> NAME/KEY: MOD_RES
<222> LOCATION: (89)..(89)
<223> OTHER INFORMATION: Ile or Arg
<220> FEATURE:
<221> NAME/KEY: MOD_RES
<222> LOCATION: (91)..(91)
<223> OTHER INFORMATION: Ile or Val
<220> FEATURE:
<221> NAME/KEY: MOD_RES
<222> LOCATION: (121)..(121)
<223> OTHER INFORMATION: Thr or Ser
<220> FEATURE:
<221> NAME/KEY: MOD_RES
<222> LOCATION: (131)..(131)
<223> OTHER INFORMATION: Thr or Pro
<220> FEATURE:
<221> NAME/KEY: MOD_RES
```

```
<222> LOCATION: (151)..(151)
<223> OTHER INFORMATION: Pro or Thr
<220> FEATURE:
<221> NAME/KEY: MOD_RES
<222> LOCATION: (169)..(169)
<223> OTHER INFORMATION: Ser or Gly
<220> FEATURE:
<221> NAME/KEY: MOD_RES
<222> LOCATION: (190)..(190)
<223> OTHER INFORMATION: Ser or Ala
<220> FEATURE:
<221> NAME/KEY: MOD_RES
<222> LOCATION: (191)..(191)
<223> OTHER INFORMATION: Arg or Gly
<220> FEATURE:
<221> NAME/KEY: MOD_RES
<222> LOCATION: (206)..(206)
<223> OTHER INFORMATION: Lys or Ile
<220> FEATURE:
<221> NAME/KEY: MOD_RES
<222> LOCATION: (210)..(210)
<223> OTHER INFORMATION: Asp or Glu
<220> FEATURE:
<221> NAME/KEY: MOD_RES
<222> LOCATION: (232)..(232)
<223> OTHER INFORMATION: Glu or Asn

<400> SEQUENCE: 30

Met Thr Tyr Pro Arg Arg Tyr Arg Arg Arg His Arg Pro Arg
1               5                   10                  15

Ser His Leu Gly Gln Ile Leu Arg Arg Pro Trp Leu Val His Pro
            20                  25                  30

Arg His Arg Tyr Arg Trp Arg Arg Lys Asn Gly Ile Phe Asn Thr Arg
        35                  40                  45

Leu Ser Arg Thr Phe Gly Tyr Thr Xaa Lys Xaa Thr Thr Val Xaa Thr
50                  55                  60

Pro Ser Trp Ala Val Asp Met Met Arg Phe Asn Ile Xaa Asp Phe Xaa
65                  70                  75                  80

Pro Pro Gly Gly Gly Xaa Asn Xaa Xaa Ser Xaa Pro Phe Glu Tyr Tyr
                85                  90                  95

Arg Ile Arg Lys Val Lys Val Glu Phe Trp Pro Cys Ser Pro Ile Thr
            100                 105                 110

Gln Gly Asp Arg Gly Val Gly Ser Xaa Ala Val Ile Leu Asp Asp Asn
        115                 120                 125

Phe Val Xaa Lys Ala Thr Ala Leu Thr Tyr Asp Pro Tyr Val Asn Tyr
    130                 135                 140

Ser Ser Arg His Thr Ile Xaa Gln Pro Phe Ser Tyr His Ser Arg Tyr
145                 150                 155                 160

Phe Thr Pro Lys Pro Val Leu Asp Xaa Thr Ile Asp Tyr Phe Gln Pro
                165                 170                 175

Asn Asn Lys Arg Asn Gln Leu Trp Leu Arg Leu Gln Thr Xaa Xaa Asn
            180                 185                 190

Val Asp His Val Gly Leu Gly Thr Ala Phe Glu Asn Ser Xaa Tyr Asp
        195                 200                 205

Gln Xaa Tyr Asn Ile Arg Val Thr Met Tyr Val Gln Phe Arg Glu Phe
    210                 215                 220

Asn Leu Lys Asp Pro Pro Leu Xaa Pro
225                 230

<210> SEQ ID NO 31
<211> LENGTH: 4
<212> TYPE: PRT
<213> ORGANISM: Unknown
```

```
<220> FEATURE:
<223> OTHER INFORMATION: Description of Unknown: Factor Xa cleavage site
      peptide

<400> SEQUENCE: 31

Ile Glu Glu Arg
1

<210> SEQ ID NO 32
<211> LENGTH: 9
<212> TYPE: PRT
<213> ORGANISM: Artificial Sequence
<220> FEATURE:
<223> OTHER INFORMATION: Description of Artificial Sequence: Synthetic
      mass-labeled peptide derived from the ORF2 protein of porcine
      circovirus (PCV)
<220> FEATURE:
<221> NAME/KEY: MOD_RES
<222> LOCATION: (1)..(1)
<223> OTHER INFORMATION: Preferably C13 and N15 isotope labeled
<220> FEATURE:
<221> NAME/KEY: MOD_RES
<222> LOCATION: (3)..(3)
<223> OTHER INFORMATION: Preferably C13 and N15 isotope labeled

<400> SEQUENCE: 32

Ile Ser Ile Pro Phe Glu Tyr Tyr Arg
1               5

<210> SEQ ID NO 33
<211> LENGTH: 14
<212> TYPE: PRT
<213> ORGANISM: Artificial Sequence
<220> FEATURE:
<223> OTHER INFORMATION: Description of Artificial Sequence: Synthetic
      mass-labeled peptide derived from the ORF2 protein of porcine
      circovirus (PCV)
<220> FEATURE:
<221> NAME/KEY: MOD_RES
<222> LOCATION: (6)..(6)
<223> OTHER INFORMATION: Cys(carboxymethyl)
<220> FEATURE:
<221> NAME/KEY: MOD_RES
<222> LOCATION: (14)..(14)
<223> OTHER INFORMATION: Preferably C13 and N15 isotope labeled

<400> SEQUENCE: 33

Val Glu Phe Trp Pro Cys Ser Pro Ile Thr Gln Gly Asp Arg
1               5                   10
```